United States Patent
Gilmore et al.

(10) Patent No.: US 10,022,114 B2
(45) Date of Patent: Jul. 17, 2018

(54) PERCUTANEOUS TETHER LOCKING

(71) Applicant: 4 TECH INC., Waltham, MA (US)

(72) Inventors: Michael Gilmore, County Galway (IE); Idan Tobis, Beth Hashmonai (IL); Charlotte Murphy, County Galway (IE); Francesco Maisano, Zürich (CH); Gareth Clarke, Limerick (IE); Kevin Lynn, County Galway (IE)

(73) Assignee: 4TECH INC., Waltham, MA (US)

( * ) Notice: Subject to any disclaimer, the term of this patent is extended or adjusted under 35 U.S.C. 154(b) by 784 days.

(21) Appl. No.: 14/525,668

(22) Filed: Oct. 28, 2014

(65) Prior Publication Data

US 2015/0119936 A1   Apr. 30, 2015

Related U.S. Application Data

(60) Provisional application No. 61/897,491, filed on Oct. 30, 2013.

(51) Int. Cl.
    *A61B 17/04*     (2006.01)
    *A61B 17/00*     (2006.01)
    *A61F 2/82*     (2013.01)

(52) U.S. Cl.
    CPC ...... *A61B 17/0401* (2013.01); *A61B 17/0487* (2013.01); *A61B 2017/00243* (2013.01);
(Continued)

(58) Field of Classification Search
    CPC ............ A61B 17/0487; A61B 17/0401; A61B 2017/0462
See application file for complete search history.

(56) References Cited

U.S. PATENT DOCUMENTS

| | | |
|---|---|---|
| 3,874,388 A | 4/1975 | King et al. |
| 4,214,349 A | 7/1980 | Munch |

(Continued)

FOREIGN PATENT DOCUMENTS

| | | |
|---|---|---|
| CN | 2398971 Y | 10/2000 |
| DE | 102007043830 A1 | 4/2009 |

(Continued)

OTHER PUBLICATIONS

First Chinese Office Action dated Jun. 30, 2014: Appln. No. 201180015301.6.
(Continued)

*Primary Examiner* — Kathleen Holwerda
*Assistant Examiner* — Christina Lauer
(74) *Attorney, Agent, or Firm* — Ultimatedge IP Law Group, P.C.; Dean G. Stathakis; Vito A. Canuso, III

(57) ABSTRACT

A tether-securing device is provided that includes a tubular element, which is shaped so as define a lateral wall that surrounds a lumen. The lateral wall is shaped so as to define a one-way locking opening. The tether-securing device further includes at least one tether, which (a) has at least a first tether end portion, and (b) passes through the lumen and the one-way locking opening. The tether-securing device additionally includes first and second tissue anchors. The first tissue anchor is connected to the first tether end portion. The one-way locking opening is configured to (a) allow sliding of the at least one tether in a first direction through the one-way locking opening, and (b) inhibit sliding of the at least one tether in a second direction opposite the first direction. Other embodiments are also described.

31 Claims, 18 Drawing Sheets

(52) U.S. Cl.
CPC ............... *A61B 2017/00783* (2013.01); *A61B 2017/0409* (2013.01); *A61B 2017/0441* (2013.01); *A61B 2017/0462* (2013.01); *A61B 2017/0464* (2013.01); *A61B 2017/0488* (2013.01); *A61B 2017/0496* (2013.01); *A61F 2/82* (2013.01)

(56) References Cited

U.S. PATENT DOCUMENTS

| | | | |
|---|---|---|---|
| 4,423,525 A | 1/1984 | Vallana et al. | |
| 4,493,329 A | 1/1985 | Crawford et al. | |
| 4,532,926 A | 8/1985 | O'Holla | |
| 4,602,911 A | 7/1986 | Ahmadi et al. | |
| 4,625,727 A | 12/1986 | Leiboff | |
| 4,778,468 A | 10/1988 | Hunt et al. | |
| 4,853,986 A | 8/1989 | Allen | |
| 5,108,420 A | 4/1992 | Marks | |
| 5,330,521 A | 7/1994 | Cohen | |
| 5,450,860 A | 9/1995 | O'Connor | |
| 5,473,812 A | 12/1995 | Morris et al. | |
| 5,474,518 A | 12/1995 | Farrer Velazquez | |
| 5,643,289 A | 7/1997 | Sauer et al. | |
| 5,776,178 A | 7/1998 | Pohndorf et al. | |
| 5,792,400 A | 8/1998 | Talja et al. | |
| 5,843,120 A | 12/1998 | Israel et al. | |
| 5,843,164 A | 12/1998 | Frantzen et al. | |
| 5,948,000 A | 9/1999 | Larsen et al. | |
| 5,957,953 A | 9/1999 | DiPoto et al. | |
| 5,961,440 A | 10/1999 | Schweich, Jr. et al. | |
| 6,024,756 A | 2/2000 | Huesbsch et al. | |
| 6,027,523 A | 2/2000 | Schmieding | |
| 6,045,497 A | 4/2000 | Schweich, Jr. et al. | |
| 6,050,936 A | 4/2000 | Schweich, Jr. et al. | |
| 6,077,214 A | 6/2000 | Mortier et al. | |
| 6,183,512 B1 | 2/2001 | Howanec, Jr. et al. | |
| 6,193,734 B1 | 2/2001 | Bolduc et al. | |
| 6,210,432 B1 | 4/2001 | Solem et al. | |
| 6,298,272 B1 | 10/2001 | Peterfeso et al. | |
| 6,299,635 B1 | 10/2001 | Frantzen | |
| 6,332,893 B1 | 12/2001 | Mortier et al. | |
| 6,338,738 B1 | 1/2002 | Bellotti et al. | |
| 6,402,780 B2 | 6/2002 | Williamson, IV et al. | |
| 6,402,781 B1 | 6/2002 | Langberg et al. | |
| 6,406,420 B1 | 6/2002 | McCarthy et al. | |
| 6,533,810 B2 | 3/2003 | Hankh et al. | |
| 6,537,198 B1 | 3/2003 | Vidlund et al. | |
| 6,537,314 B2 | 3/2003 | Langberg et al. | |
| 6,575,976 B2 | 6/2003 | Grafton | |
| 6,585,766 B1 | 7/2003 | Huynh et al. | |
| 6,602,288 B1 | 8/2003 | Cosgrove et al. | |
| 6,613,078 B1 | 9/2003 | Barone | |
| 6,613,079 B1 | 9/2003 | Wolinsky et al. | |
| 6,616,684 B1 | 9/2003 | Vidlund et al. | |
| 6,619,291 B2 | 9/2003 | Hlavka et al. | |
| 6,622,730 B2 | 9/2003 | Ekvall et al. | |
| 6,626,899 B2 | 9/2003 | Houser et al. | |
| 6,626,930 B1 | 9/2003 | Allen et al. | |
| 6,629,534 B1 | 10/2003 | St. Goar et al. | |
| 6,629,921 B1 | 10/2003 | Schweich, Jr. et al. | |
| 6,641,597 B2 | 11/2003 | Burkhart et al. | |
| 6,645,193 B2 | 11/2003 | Mangosong | |
| 6,702,846 B2 | 3/2004 | Mikus et al. | |
| 6,709,456 B2 | 3/2004 | Langberg et al. | |
| 6,718,985 B2 | 4/2004 | Hlavka et al. | |
| 6,719,767 B1 | 4/2004 | Kimblad | |
| 6,723,038 B1 | 4/2004 | Schroeder et al. | |
| 6,730,118 B2 | 5/2004 | Spenser et al. | |
| 6,743,198 B1 | 6/2004 | Tihon | |
| 6,746,472 B2 | 6/2004 | Frazier et al. | |
| 6,764,510 B2 | 7/2004 | Vidlund et al. | |
| 6,776,754 B1 | 8/2004 | Wilk | |
| 6,797,001 B2 | 9/2004 | Mathis et al. | |
| 6,810,882 B2 | 11/2004 | Langberg et al. | |
| 6,884,250 B2 | 4/2005 | Monassevitch et al. | |
| 6,893,459 B1 | 5/2005 | Macoviak | |
| 6,908,478 B2 | 6/2005 | Alferness et al. | |
| 6,929,660 B1 | 8/2005 | Ainsworth et al. | |
| 6,989,028 B2 | 1/2006 | Lashinski et al. | |
| 6,997,951 B2 | 2/2006 | Solem et al. | |
| 7,011,682 B2 | 3/2006 | Lashinski et al. | |
| 7,041,097 B1 | 5/2006 | Webler | |
| 7,044,967 B2 | 5/2006 | Solem et al. | |
| 7,056,333 B2 | 6/2006 | Walshe | |
| 7,063,711 B1 | 6/2006 | Loshakove et al. | |
| 7,077,861 B2 | 7/2006 | Spence | |
| 7,083,628 B2 | 8/2006 | Bachman | |
| 7,087,064 B1 | 8/2006 | Hyde | |
| 7,094,244 B2 | 8/2006 | Schreck | |
| 7,101,395 B2 | 9/2006 | Tremulis et al. | |
| 7,101,396 B2 | 9/2006 | Artof et al. | |
| 7,112,219 B2 | 9/2006 | Vidlund et al. | |
| 7,125,421 B2 | 10/2006 | Tremulis et al. | |
| 7,144,363 B2 | 12/2006 | Pai et al. | |
| 7,159,593 B2 | 1/2007 | McCarthy et al. | |
| 7,166,127 B2 | 1/2007 | Spence et al. | |
| 7,169,187 B2 | 1/2007 | Datta et al. | |
| 7,175,625 B2 | 2/2007 | Culbert | |
| 7,186,262 B2 | 3/2007 | Saadat | |
| 7,189,199 B2 | 3/2007 | McCarthy et al. | |
| 7,192,442 B2 | 3/2007 | Solem et al. | |
| 7,192,443 B2 | 3/2007 | Solem et al. | |
| 7,201,772 B2 | 4/2007 | Schwammenthal et al. | |
| 7,211,110 B2 | 5/2007 | Rowe et al. | |
| 7,241,257 B1 | 7/2007 | Ainsworth et al. | |
| 7,247,134 B2 | 7/2007 | Vidlund et al. | |
| 7,258,697 B1 | 8/2007 | Cox et al. | |
| 7,291,168 B2 | 11/2007 | Macoviak et al. | |
| 7,311,728 B2 | 12/2007 | Solem et al. | |
| 7,316,706 B2 | 1/2008 | Bloom et al. | |
| 7,316,710 B1 | 1/2008 | Cheng et al. | |
| 7,329,279 B2 | 2/2008 | Haug et al. | |
| 7,331,972 B1 | 2/2008 | Cox | |
| 7,335,213 B1 | 2/2008 | Hyde et al. | |
| 7,338,506 B2 | 3/2008 | Caro | |
| 7,351,256 B2 | 4/2008 | Hojeibane et al. | |
| 7,371,244 B2 | 5/2008 | Chatlynne et al. | |
| 7,374,573 B2 | 5/2008 | Gabbay | |
| 7,381,210 B2 | 6/2008 | Zarbatany et al. | |
| 7,381,220 B2 | 6/2008 | Macoviak et al. | |
| 7,390,329 B2 | 6/2008 | Westra et al. | |
| 7,431,692 B2 | 10/2008 | Zollinger et al. | |
| 7,431,726 B2 | 10/2008 | Spence et al. | |
| 7,485,143 B2 | 2/2009 | Webler et al. | |
| 7,500,989 B2 | 3/2009 | Solem et al. | |
| 7,503,931 B2 | 3/2009 | Kowalsky et al. | |
| 7,510,575 B2 | 3/2009 | Spenser et al. | |
| 7,527,646 B2 | 5/2009 | Rahdert et al. | |
| 7,530,995 B2 | 5/2009 | Quijano et al. | |
| 7,547,321 B2 | 6/2009 | Silvestri et al. | |
| 7,549,983 B2 | 6/2009 | Roue et al. | |
| 7,608,102 B2 | 10/2009 | Adams et al. | |
| 7,618,449 B2 | 11/2009 | Tremulis et al. | |
| 7,628,797 B2 | 12/2009 | Tieu et al. | |
| 7,632,303 B1 | 12/2009 | Stalker et al. | |
| 7,637,946 B2 | 12/2009 | Solem et al. | |
| 7,655,040 B2 | 2/2010 | Douk et al. | |
| 7,666,204 B2 | 2/2010 | Thornton et al. | |
| 7,695,512 B2 | 4/2010 | Lashinski et al. | |
| 7,704,277 B2 | 4/2010 | Zakay et al. | |
| 7,722,523 B2 | 5/2010 | Mortier et al. | |
| 7,736,378 B2 * | 6/2010 | Maahs ............... A61B 17/0401 606/232 |
| 7,758,632 B2 | 7/2010 | Hojeibane et al. | |
| 7,766,816 B2 | 8/2010 | Chin et al. | |
| 7,771,467 B2 | 8/2010 | Svensson | |
| 7,780,702 B2 * | 8/2010 | Shiono ............... A61B 17/0401 606/151 |
| 7,780,726 B2 | 8/2010 | Seguin | |
| 7,785,366 B2 | 8/2010 | Maurer et al. | |
| 7,803,187 B2 | 9/2010 | Hauser | |
| 7,806,910 B2 | 10/2010 | Anderson | |
| 7,841,502 B2 | 11/2010 | Walberg et al. | |
| 7,871,433 B2 | 1/2011 | Lattouf | |
| 7,883,539 B2 | 2/2011 | Schweich, Jr. et al. | |

(56) References Cited

U.S. PATENT DOCUMENTS

| | | |
|---|---|---|
| 7,892,214 B2 | 2/2011 | Kagan et al. |
| 7,930,016 B1 | 4/2011 | Saadat |
| 7,947,207 B2 | 5/2011 | McNiven et al. |
| 7,988,725 B2 | 8/2011 | Gross et al. |
| 7,991,484 B1 | 8/2011 | Sengupta et al. |
| 7,992,567 B2 | 8/2011 | Hirotsuka et al. |
| 7,993,368 B2 | 8/2011 | Gambale et al. |
| 7,993,397 B2 | 8/2011 | Lashinski et al. |
| 8,010,207 B2 | 8/2011 | Smits et al. |
| 8,029,518 B2 | 10/2011 | Goldfarb et al. |
| 8,052,592 B2 | 11/2011 | Goldfarb et al. |
| 8,075,616 B2 | 12/2011 | Solem et al. |
| 8,092,520 B2 | 1/2012 | Quadri |
| 8,092,525 B2 | 1/2012 | Eliasen et al. |
| 8,100,820 B2 | 1/2012 | Hauser et al. |
| 8,108,054 B2 | 1/2012 | Helland |
| 8,142,493 B2 | 3/2012 | Spence et al. |
| 8,142,495 B2 | 3/2012 | Hasenkam et al. |
| 8,157,810 B2 | 4/2012 | Case et al. |
| 8,202,281 B2 | 6/2012 | Voss |
| 8,202,315 B2 | 6/2012 | Hlavka et al. |
| 8,216,302 B2 | 7/2012 | Wilson et al. |
| 8,226,707 B2 | 7/2012 | White |
| 8,236,013 B2 | 8/2012 | Chu |
| 8,236,049 B2 | 8/2012 | Rowe et al. |
| 8,252,005 B2 | 8/2012 | Findlay, III et al. |
| 8,262,567 B2 | 9/2012 | Sharp et al. |
| 8,262,724 B2 | 9/2012 | Seguin et al. |
| 8,262,725 B2 | 9/2012 | Subramanian |
| 8,267,981 B2 | 9/2012 | Boock et al. |
| 8,313,497 B2 | 11/2012 | Walberg et al. |
| 8,313,498 B2 | 11/2012 | Pantages et al. |
| 8,323,312 B2 | 12/2012 | Clark |
| 8,323,335 B2 | 12/2012 | Rowe et al. |
| 8,332,051 B2 | 12/2012 | Sommer et al. |
| 8,361,088 B2 | 1/2013 | McIntosh |
| 8,382,829 B1 | 2/2013 | Call et al. |
| 8,394,008 B2 | 3/2013 | Annest et al. |
| 8,398,672 B2 | 3/2013 | Kleshinski et al. |
| 8,409,273 B2 | 4/2013 | Thornton et al. |
| 8,419,753 B2 | 4/2013 | Stafford |
| 8,430,893 B2 | 4/2013 | Ma |
| 8,449,606 B2 | 5/2013 | Eliasen et al. |
| 8,460,368 B2 | 6/2013 | Taylor et al. |
| 8,460,371 B2 | 6/2013 | Hlavka et al. |
| 8,475,525 B2 | 7/2013 | Maisano et al. |
| 8,480,691 B2 | 7/2013 | Dana et al. |
| 8,480,730 B2 | 7/2013 | Maurer et al. |
| 8,518,107 B2 | 8/2013 | Tsukashima et al. |
| 8,523,881 B2 | 9/2013 | Cabiri et al. |
| 8,524,132 B2 | 9/2013 | Von Oepen et al. |
| 8,529,621 B2 | 9/2013 | Alfieri et al. |
| 8,545,553 B2 | 10/2013 | Zipory et al. |
| 8,568,475 B2 | 10/2013 | Nguyen et al. |
| 8,568,476 B2 | 10/2013 | Rao et al. |
| 8,591,460 B2 | 11/2013 | Wilson et al. |
| 8,597,347 B2 | 12/2013 | Maurer et al. |
| 8,628,569 B2 | 1/2014 | Benichou et al. |
| 8,628,571 B1 | 1/2014 | Hacohen et al. |
| 8,647,368 B2 * | 2/2014 | Ducharme ......... A61B 17/0057 606/232 |
| 8,663,248 B2 | 3/2014 | Zung et al. |
| 8,685,080 B2 | 4/2014 | White |
| 8,685,083 B2 | 4/2014 | Perier et al. |
| 8,728,097 B1 | 5/2014 | Sugimoto et al. |
| 8,747,463 B2 | 6/2014 | Fogarty et al. |
| 8,753,357 B2 | 6/2014 | Roorda et al. |
| 8,753,373 B2 | 6/2014 | Chau et al. |
| 8,758,402 B2 | 6/2014 | Jenson et al. |
| 8,778,017 B2 | 7/2014 | Eliasen et al. |
| 8,784,481 B2 | 7/2014 | Alkhatib et al. |
| 8,790,394 B2 | 7/2014 | Miller et al. |
| 8,795,356 B2 | 8/2014 | Quadri et al. |
| 8,808,366 B2 | 8/2014 | Braido et al. |
| 8,808,368 B2 | 8/2014 | Maisano et al. |
| 8,845,723 B2 | 9/2014 | Spence et al. |
| 8,852,270 B2 | 10/2014 | Maurer et al. |
| 8,858,594 B2 | 10/2014 | Clark |
| 8,858,623 B2 | 10/2014 | Miller et al. |
| 8,864,822 B2 | 10/2014 | Spence et al. |
| 8,870,949 B2 | 10/2014 | Rowe |
| 8,870,950 B2 | 10/2014 | Hacohen |
| 8,893,947 B2 | 11/2014 | Reynolds et al. |
| 8,911,461 B2 | 12/2014 | Traynor et al. |
| 8,926,691 B2 | 1/2015 | Chau et al. |
| 8,945,177 B2 | 2/2015 | Dell et al. |
| 8,945,211 B2 | 2/2015 | Sugimoto |
| 8,951,285 B2 | 2/2015 | Sugimoto et al. |
| 8,961,594 B2 | 2/2015 | Maisano et al. |
| 8,961,596 B2 * | 2/2015 | Maisano ............ A61B 17/0401 623/1.36 |
| 8,968,335 B2 | 3/2015 | Robinson et al. |
| 8,968,336 B2 | 3/2015 | Conklin et al. |
| 8,968,395 B2 | 3/2015 | Hauser et al. |
| 8,979,750 B2 | 3/2015 | Van Bladel et al. |
| 8,979,922 B2 | 3/2015 | Jayasinghe et al. |
| 8,979,923 B2 | 3/2015 | Spence et al. |
| 9,005,273 B2 | 4/2015 | Salahieh et al. |
| 9,011,468 B2 | 4/2015 | Ketai et al. |
| 9,017,347 B2 | 4/2015 | Oba et al. |
| 9,107,749 B2 | 4/2015 | Bobo et al. |
| 8,961,595 B2 | 5/2015 | Alkhatib |
| 9,034,032 B2 | 5/2015 | McLean et al. |
| 9,078,652 B2 | 7/2015 | Conklin et al. |
| 9,084,676 B2 | 7/2015 | Chau et al. |
| 9,131,939 B1 | 9/2015 | Call et al. |
| 9,138,335 B2 | 9/2015 | Cartledge et al. |
| 9,180,005 B1 | 11/2015 | Lashinski et al. |
| 9,192,471 B2 | 11/2015 | Bolling |
| 9,211,115 B2 | 12/2015 | Annest et al. |
| 9,211,203 B2 | 12/2015 | Pike et al. |
| 9,241,706 B2 | 1/2016 | Paraschac et al. |
| 9,259,218 B2 | 2/2016 | Robinson |
| 9,259,317 B2 | 2/2016 | Wilson et al. |
| 9,282,965 B2 | 3/2016 | Kokish |
| 9,289,282 B2 | 3/2016 | Olson et al. |
| 9,289,297 B2 | 3/2016 | Wilson et al. |
| 9,301,749 B2 | 4/2016 | Rowe et al. |
| 9,314,242 B2 | 4/2016 | Bachman |
| 9,358,111 B2 | 6/2016 | Spence et al. |
| 9,408,607 B2 | 8/2016 | Cartledge et al. |
| 9,474,605 B2 | 10/2016 | Rowe et al. |
| 9,662,212 B2 | 5/2017 | Van Bladel et al. |
| 2001/0018611 A1 | 8/2001 | Salem et al. |
| 2002/0013571 A1 | 1/2002 | Goldfarb et al. |
| 2002/0032481 A1 | 3/2002 | Gabbay |
| 2002/0107564 A1 | 8/2002 | Cox et al. |
| 2002/0151961 A1 | 10/2002 | Lashinski et al. |
| 2002/0177904 A1 | 11/2002 | Huxel et al. |
| 2003/0033003 A1 | 2/2003 | Harrison et al. |
| 2003/0057156 A1 | 3/2003 | Peterson et al. |
| 2003/0083742 A1 | 5/2003 | Spence et al. |
| 2003/0093096 A1 | 5/2003 | McGuckin, Jr. et al. |
| 2003/0167071 A1 | 9/2003 | Martin et al. |
| 2003/0229350 A1 | 12/2003 | Kay |
| 2003/0229361 A1 | 12/2003 | Jackson |
| 2003/0236568 A1 | 12/2003 | Hojeibane et al. |
| 2004/0117009 A1 | 6/2004 | Cali et al. |
| 2004/0133274 A1 | 7/2004 | Webler et al. |
| 2004/0172046 A1 | 9/2004 | Hlavka et al. |
| 2004/0181287 A1 | 9/2004 | Gellman |
| 2004/0186566 A1 | 9/2004 | Hindrichs et al. |
| 2004/0193092 A1 | 9/2004 | Deal |
| 2004/0236372 A1 * | 11/2004 | Anspach, III ...... A61B 17/0487 606/232 |
| 2004/0236419 A1 | 11/2004 | Milo |
| 2004/0260389 A1 | 12/2004 | Case et al. |
| 2005/0016560 A1 | 1/2005 | Voughlohn |
| 2005/0055089 A1 | 3/2005 | Macoviak et al. |
| 2005/0059934 A1 | 3/2005 | Chanduszko et al. |
| 2005/0065434 A1 | 3/2005 | Bavaro et al. |
| 2005/0075723 A1 | 4/2005 | Schroeder et al. |
| 2005/0090827 A1 | 4/2005 | Gedebou |
| 2005/0107812 A1 | 5/2005 | Starksen et al. |

(56) References Cited

U.S. PATENT DOCUMENTS

| | | |
|---|---|---|
| 2005/0107871 A1 | 5/2005 | Realyvasquez et al. |
| 2005/0137686 A1 | 6/2005 | Salahieh et al. |
| 2005/0137688 A1 | 6/2005 | Salahieh et al. |
| 2005/0143770 A1 | 6/2005 | Carter et al. |
| 2005/0149182 A1 | 7/2005 | Alferness et al. |
| 2005/0154448 A1 | 7/2005 | Cully et al. |
| 2005/0171601 A1 | 8/2005 | Cosgrove et al. |
| 2005/0177180 A1 | 8/2005 | Kaganov et al. |
| 2005/0177228 A1 | 8/2005 | Solem et al. |
| 2005/0203606 A1 | 9/2005 | Vancamp |
| 2005/0216039 A1 | 9/2005 | Lederman |
| 2005/0216079 A1 | 9/2005 | MaCoviak |
| 2005/0222488 A1 | 10/2005 | Chang et al. |
| 2005/0222665 A1 | 10/2005 | Aranyi |
| 2005/0228422 A1 | 10/2005 | Machold et al. |
| 2005/0251208 A1 | 11/2005 | Elmer et al. |
| 2005/0273138 A1 | 12/2005 | To et al. |
| 2006/0004442 A1 | 1/2006 | Spenser et al. |
| 2006/0020326 A9 | 1/2006 | Bolduc et al. |
| 2006/0020327 A1 | 1/2006 | Lashinski et al. |
| 2006/0020335 A1 | 1/2006 | Kowalsky et al. |
| 2006/0052821 A1 | 3/2006 | Abbott et al. |
| 2006/0079736 A1 | 4/2006 | Chin et al. |
| 2006/0106278 A1 | 5/2006 | Machold et al. |
| 2006/0106279 A1 | 5/2006 | Machold et al. |
| 2006/0106423 A1 | 5/2006 | Weisel et al. |
| 2006/0129166 A1 | 6/2006 | Lavelle |
| 2006/0161265 A1 | 7/2006 | Levine et al. |
| 2006/0173524 A1 | 8/2006 | Salahieh et al. |
| 2006/0178700 A1 | 8/2006 | Quinn |
| 2006/0200199 A1 | 9/2006 | Bonutti et al. |
| 2006/0229708 A1 | 10/2006 | Powell et al. |
| 2006/0241745 A1 | 10/2006 | Solem |
| 2006/0241748 A1 | 10/2006 | Lee et al. |
| 2006/0252984 A1 | 11/2006 | Rahdert et al. |
| 2006/0259044 A1 | 11/2006 | Onuki et al. |
| 2006/0259135 A1 | 11/2006 | Navia et al. |
| 2006/0265042 A1 | 11/2006 | Catanese, III et al. |
| 2006/0276871 A1 | 12/2006 | Lamson et al. |
| 2006/0282161 A1 | 12/2006 | Huynh et al. |
| 2007/0005081 A1 | 1/2007 | Findlay, III et al. |
| 2007/0010829 A1 | 1/2007 | Nobles et al. |
| 2007/0016287 A1 | 1/2007 | Cartledge et al. |
| 2007/0016288 A1 | 1/2007 | Gurskis et al. |
| 2007/0021781 A1 | 1/2007 | Jervis et al. |
| 2007/0032787 A1 | 2/2007 | Hassett et al. |
| 2007/0032796 A1 | 2/2007 | Chin-Chen et al. |
| 2007/0032820 A1 | 2/2007 | Chin-Chen et al. |
| 2007/0038221 A1 | 2/2007 | Fine et al. |
| 2007/0038296 A1 | 2/2007 | Navia et al. |
| 2007/0049942 A1 | 3/2007 | Hindrichs et al. |
| 2007/0049970 A1 | 3/2007 | Belef et al. |
| 2007/0049971 A1 | 3/2007 | Chin et al. |
| 2007/0051377 A1 | 3/2007 | Douk et al. |
| 2007/0055340 A1 | 3/2007 | Pryor |
| 2007/0060989 A1 | 3/2007 | Deem et al. |
| 2007/0061010 A1 | 3/2007 | Hauser et al. |
| 2007/0066863 A1 | 3/2007 | Rafiee et al. |
| 2007/0083168 A1 | 4/2007 | Whiting et al. |
| 2007/0093869 A1 | 4/2007 | Bloom et al. |
| 2007/0100427 A1 | 5/2007 | Perouse |
| 2007/0112425 A1 | 5/2007 | Schaller et al. |
| 2007/0118151 A1 | 5/2007 | Davidson |
| 2007/0162107 A1 | 7/2007 | Haug et al. |
| 2007/0168013 A1 | 7/2007 | Douglas |
| 2007/0179530 A1 | 8/2007 | Tieu et al. |
| 2007/0185532 A1 | 8/2007 | Stone et al. |
| 2007/0198082 A1 | 8/2007 | Kapadia et al. |
| 2007/0203391 A1 | 8/2007 | Bloom et al. |
| 2007/0208389 A1 | 9/2007 | Amundson et al. |
| 2007/0219558 A1 | 9/2007 | Deutsch |
| 2007/0250160 A1 | 10/2007 | Rafiee |
| 2007/0265658 A1 | 11/2007 | Nelson et al. |
| 2007/0265700 A1 | 11/2007 | Eliasen et al. |
| 2007/0270943 A1 | 11/2007 | Solem et al. |
| 2007/0276437 A1 | 11/2007 | Call et al. |
| 2007/0282375 A1 | 12/2007 | Hindrichs et al. |
| 2007/0282429 A1 | 12/2007 | Hauser et al. |
| 2007/0288086 A1 | 12/2007 | Kalmann et al. |
| 2007/0288089 A1 | 12/2007 | Gurskis et al. |
| 2008/0003539 A1 | 1/2008 | Lundgren |
| 2008/0027268 A1 | 1/2008 | Buckner et al. |
| 2008/0027446 A1 | 1/2008 | Stone et al. |
| 2008/0027483 A1 | 1/2008 | Cartledge et al. |
| 2008/0033475 A1 | 2/2008 | Meng |
| 2008/0035160 A1 | 2/2008 | Woodson et al. |
| 2008/0039845 A1 | 2/2008 | Bonutti et al. |
| 2008/0077231 A1 | 3/2008 | Heringes et al. |
| 2008/0091264 A1 | 4/2008 | Machold et al. |
| 2008/0097595 A1 | 4/2008 | Gabbay |
| 2008/0125861 A1 | 5/2008 | Webler et al. |
| 2008/0140116 A1 | 6/2008 | Bonutti |
| 2008/0140188 A1 | 6/2008 | Rahdert et al. |
| 2008/0167714 A1 | 7/2008 | St. Goar et al. |
| 2008/0234729 A1 | 9/2008 | Page et al. |
| 2008/0262609 A1 | 10/2008 | Gross et al. |
| 2008/0275469 A1 | 11/2008 | Fanton et al. |
| 2008/0281411 A1 | 11/2008 | Berreklouw |
| 2008/0288044 A1 | 11/2008 | Osborne |
| 2008/0288062 A1 | 11/2008 | Andrieu et al. |
| 2008/0300629 A1 | 12/2008 | Surti |
| 2009/0005792 A1 | 1/2009 | Miyamoto et al. |
| 2009/0082828 A1 | 3/2009 | Ostroff |
| 2009/0082847 A1 | 3/2009 | Zacharias et al. |
| 2009/0084386 A1 | 4/2009 | McClellan |
| 2009/0099649 A1 | 4/2009 | Chobotov et al. |
| 2009/0118776 A1 | 5/2009 | Kelsch et al. |
| 2009/0143808 A1 | 6/2009 | Houser |
| 2009/0149872 A1 | 6/2009 | Gross et al. |
| 2009/0171439 A1 | 7/2009 | Nissl |
| 2009/0216265 A1 | 8/2009 | DeVries et al. |
| 2009/0254103 A1 | 10/2009 | Deutsch |
| 2009/0259307 A1 | 10/2009 | Gross et al. |
| 2009/0264995 A1 | 10/2009 | Subramanian |
| 2009/0276040 A1 | 11/2009 | Rowe et al. |
| 2009/0287304 A1 | 11/2009 | Dahlgren et al. |
| 2009/0306622 A1 | 12/2009 | Machold et al. |
| 2009/0326648 A1 | 12/2009 | Machold et al. |
| 2010/0023117 A1 | 1/2010 | Yoganathan et al. |
| 2010/0023118 A1 | 1/2010 | Medlock et al. |
| 2010/0029071 A1 | 2/2010 | Russell et al. |
| 2010/0030329 A1 | 2/2010 | Frater |
| 2010/0049293 A1 | 2/2010 | Zukowski et al. |
| 2010/0063542 A1 | 3/2010 | van der Burg et al. |
| 2010/0063586 A1 | 3/2010 | Hasenkam et al. |
| 2010/0121349 A1 | 5/2010 | Meier et al. |
| 2010/0121434 A1 | 5/2010 | Paul et al. |
| 2010/0121435 A1 | 5/2010 | Subramanian et al. |
| 2010/0130992 A1 | 5/2010 | Machold et al. |
| 2010/0161041 A1 | 6/2010 | Maisano et al. |
| 2010/0161042 A1 | 6/2010 | Maisano et al. |
| 2010/0161043 A1 | 6/2010 | Maisano et al. |
| 2010/0161047 A1 | 6/2010 | Cabiri |
| 2010/0168791 A1 | 7/2010 | Kassab et al. |
| 2010/0174358 A1 | 7/2010 | Rabkin et al. |
| 2010/0185278 A1 | 7/2010 | Schankereli |
| 2010/0204662 A1 | 8/2010 | Orlov et al. |
| 2010/0211166 A1 | 8/2010 | Miller et al. |
| 2010/0217309 A1 | 8/2010 | Hansen et al. |
| 2010/0217382 A1 | 8/2010 | Chau et al. |
| 2010/0228269 A1 | 9/2010 | Garrison et al. |
| 2010/0249908 A1 | 9/2010 | Chau et al. |
| 2010/0249920 A1 | 9/2010 | Bolling et al. |
| 2010/0256690 A1 | 10/2010 | Appenzeller et al. |
| 2010/0280603 A1 | 11/2010 | Maisano et al. |
| 2010/0280604 A1 | 11/2010 | Zipory et al. |
| 2010/0280605 A1 | 11/2010 | Hammer et al. |
| 2010/0286628 A1 | 11/2010 | Gross |
| 2010/0286767 A1 | 11/2010 | Zipory et al. |
| 2010/0298930 A1 | 11/2010 | Orlov |
| 2010/0324598 A1 | 12/2010 | Anderson |
| 2011/0004296 A1 | 1/2011 | Lutter et al. |
| 2011/0011917 A1 | 1/2011 | Loulmet |
| 2011/0022164 A1 | 1/2011 | Quinn et al. |

(56) References Cited

U.S. PATENT DOCUMENTS

| | | |
|---|---|---|
| 2011/0029066 A1 | 2/2011 | Gilad et al. |
| 2011/0029071 A1 | 2/2011 | Zlotnick et al. |
| 2011/0035000 A1 | 2/2011 | Nieminen et al. |
| 2011/0040366 A1 | 2/2011 | Goetz et al. |
| 2011/0071626 A1 | 3/2011 | Wright et al. |
| 2011/0077733 A1 | 3/2011 | Solem |
| 2011/0082538 A1 | 4/2011 | Dahlgren et al. |
| 2011/0087146 A1 | 4/2011 | Ryan et al. |
| 2011/0093002 A1 | 4/2011 | Rucker et al. |
| 2011/0106245 A1 | 5/2011 | Miller et al. |
| 2011/0106247 A1 | 5/2011 | Miller et al. |
| 2011/0112619 A1 | 5/2011 | Foster et al. |
| 2011/0112632 A1 | 5/2011 | Chau et al. |
| 2011/0184510 A1 | 7/2011 | Maisano et al. |
| 2011/0190879 A1 | 8/2011 | Bobo et al. |
| 2011/0208283 A1 | 8/2011 | Rust |
| 2011/0224785 A1 | 9/2011 | Hacohen |
| 2011/0238088 A1 | 9/2011 | Bolduc et al. |
| 2011/0238112 A1 | 9/2011 | Kim et al. |
| 2011/0251641 A1 | 10/2011 | Sauer et al. |
| 2011/0251678 A1 | 10/2011 | Eidenschink et al. |
| 2011/0264208 A1 | 10/2011 | Duffy et al. |
| 2011/0288635 A1* | 11/2011 | Miller ............... A61B 17/0401 623/2.1 |
| 2011/0301698 A1 | 12/2011 | Miller et al. |
| 2012/0016343 A1 | 1/2012 | Gill |
| 2012/0022633 A1 | 1/2012 | Olson et al. |
| 2012/0022639 A1 | 1/2012 | Hacohen et al. |
| 2012/0022640 A1 | 1/2012 | Gross et al. |
| 2012/0035712 A1 | 2/2012 | Maisano et al. |
| 2012/0083806 A1 | 4/2012 | Goertzen |
| 2012/0123531 A1 | 5/2012 | Tsukashima et al. |
| 2012/0179244 A1 | 7/2012 | Schankereli et al. |
| 2012/0215236 A1 | 8/2012 | Matsunaga et al. |
| 2012/0222969 A1 | 9/2012 | Osborne et al. |
| 2012/0226349 A1 | 9/2012 | Tuval et al. |
| 2012/0232373 A1 | 9/2012 | Hallander et al. |
| 2012/0245604 A1 | 9/2012 | Tegzes |
| 2012/0283757 A1 | 11/2012 | Miller et al. |
| 2012/0296349 A1 | 11/2012 | Smith et al. |
| 2013/0030522 A1 | 1/2013 | Rowe et al. |
| 2013/0325115 A1 | 1/2013 | Maisano et al. |
| 2013/0053951 A1 | 2/2013 | Ruyra Baliarda |
| 2013/0079873 A1 | 3/2013 | Migliazza et al. |
| 2013/0085529 A1 | 4/2013 | Housman |
| 2013/0096664 A1 | 4/2013 | Goetz et al. |
| 2013/0096672 A1 | 4/2013 | Reich et al. |
| 2013/0110230 A1 | 5/2013 | Solem |
| 2013/0166017 A1 | 6/2013 | Cartledge et al. |
| 2013/0166022 A1 | 6/2013 | Conklin |
| 2013/0172978 A1 | 7/2013 | Vidlund et al. |
| 2013/0190863 A1 | 7/2013 | Call et al. |
| 2013/0231701 A1 | 9/2013 | Voss et al. |
| 2013/0281760 A1 | 10/2013 | Farnan et al. |
| 2013/0325110 A1 | 12/2013 | Khalil et al. |
| 2013/0331930 A1 | 12/2013 | Rowe et al. |
| 2014/0018911 A1 | 1/2014 | Zhou et al. |
| 2014/0031864 A1 | 1/2014 | Jafari et al. |
| 2014/0031928 A1 | 1/2014 | Murphy et al. |
| 2014/0058405 A1 | 2/2014 | Foster |
| 2014/0066693 A1 | 3/2014 | Goldfarb et al. |
| 2014/0067054 A1 | 3/2014 | Chau et al. |
| 2014/0114390 A1 | 4/2014 | Tobis et al. |
| 2014/0121763 A1 | 5/2014 | Duffy et al. |
| 2014/0142689 A1 | 5/2014 | De Canniere et al. |
| 2014/0200657 A1 | 7/2014 | Maurer et al. |
| 2014/0214259 A1 | 7/2014 | Vidlund et al. |
| 2014/0243894 A1 | 8/2014 | Groothuis et al. |
| 2014/0275757 A1 | 9/2014 | Goodwin et al. |
| 2014/0277390 A1 | 9/2014 | Ratz et al. |
| 2014/0277427 A1 | 9/2014 | Ratz et al. |
| 2014/0296962 A1 | 10/2014 | Cartledge et al. |
| 2014/0309730 A1 | 10/2014 | Alon et al. |
| 2014/0324164 A1 | 10/2014 | Gross et al. |
| 2014/0358224 A1 | 12/2014 | Tegels et al. |
| 2014/0371843 A1 | 12/2014 | Wilson et al. |
| 2014/0379074 A1 | 12/2014 | Spence et al. |
| 2014/0379076 A1 | 12/2014 | Vidlund et al. |
| 2015/0045879 A1 | 2/2015 | Longoria et al. |
| 2015/0051698 A1 | 2/2015 | Ruyra Baliarda et al. |
| 2015/0066082 A1 | 3/2015 | Moshe et al. |
| 2015/0066138 A1 | 3/2015 | Alexander et al. |
| 2015/0094800 A1 | 4/2015 | Chawla |
| 2015/0100116 A1 | 4/2015 | Mohl et al. |
| 2015/0127097 A1 | 5/2015 | Neumann et al. |
| 2015/0142049 A1 | 5/2015 | Delgado et al. |
| 2015/0142103 A1 | 5/2015 | Vidlund |
| 2015/0142105 A1 | 5/2015 | Bolling et al. |
| 2015/0182336 A1 | 7/2015 | Zipory et al. |
| 2015/0196693 A1 | 7/2015 | Lin |
| 2015/0320414 A1 | 11/2015 | Conklin et al. |
| 2015/0351909 A1 | 12/2015 | Bobo, Jr. et al. |
| 2016/0022417 A1 | 1/2016 | Karapetian et al. |
| 2016/0022422 A1 | 1/2016 | Annest et al. |
| 2016/0038285 A1 | 2/2016 | Glenn et al. |
| 2016/0081829 A1 | 3/2016 | Rowe |
| 2016/0120672 A1 | 5/2016 | Martin et al. |
| 2016/0128689 A1 | 5/2016 | Sutherland et al. |
| 2016/0157862 A1 | 6/2016 | Hernandez et al. |
| 2016/0174979 A1 | 6/2016 | Wei |
| 2016/0228246 A1 | 8/2016 | Zimmerman |
| 2016/0228252 A1 | 8/2016 | Keidar |
| 2016/0235526 A1 | 8/2016 | Lashinski et al. |
| 2016/0256269 A1 | 9/2016 | Cahalane et al. |
| 2016/0270776 A1 | 9/2016 | Miraki et al. |
| 2016/0270916 A1 | 9/2016 | Cahalane et al. |
| 2016/0287383 A1 | 10/2016 | Rowe |
| 2016/0287387 A1 | 10/2016 | Wei |

FOREIGN PATENT DOCUMENTS

| | | |
|---|---|---|
| EP | 1357843 B1 | 11/2003 |
| EP | 1397176 B1 | 3/2004 |
| EP | 1562522 B1 | 8/2005 |
| EP | 1646332 B1 | 4/2006 |
| EP | 1718249 B1 | 11/2006 |
| EP | 1759663 A2 | 3/2007 |
| EP | 1836971 A2 | 9/2007 |
| EP | 1928357 B1 | 6/2008 |
| EP | 1968491 B1 | 9/2008 |
| EP | 2023858 B1 | 2/2009 |
| EP | 2399549 B1 | 12/2011 |
| EP | 2410948 B1 | 2/2012 |
| EP | 2465568 B1 | 6/2012 |
| ER | 1568326 A1 | 8/2005 |
| FR | 2930137 A1 | 10/2009 |
| JP | 2006-520651 A | 9/2006 |
| WO | 92/05093 A1 | 4/1992 |
| WO | 2004/069055 A2 | 8/2004 |
| WO | 2004/082538 A2 | 9/2004 |
| WO | 2005/012063 A2 | 3/2005 |
| WO | 2005/058206 A1 | 6/2005 |
| WO | 2005/102194 A2 | 11/2005 |
| WO | 2006/019498 A2 | 2/2006 |
| WO | 2006/097931 A2 | 9/2006 |
| WO | 2006/105008 A1 | 10/2006 |
| WO | 2006/105009 A1 | 10/2006 |
| WO | 2007/080595 A2 | 7/2007 |
| WO | 2007/140309 A2 | 12/2007 |
| WO | 2008/065044 A1 | 6/2008 |
| WO | 2008/068756 A2 | 6/2008 |
| WO | 2009/039400 A1 | 3/2009 |
| WO | 2009/101617 A2 | 8/2009 |
| WO | 2010/004546 A1 | 1/2010 |
| WO | 2010/071494 A1 | 6/2010 |
| WO | 2010/073246 A2 | 7/2010 |
| WO | 2010/099032 A2 | 9/2010 |
| WO | 2010/108079 A1 | 9/2010 |
| WO | 2010/128502 A1 | 11/2010 |
| WO | 2010/128503 A2 | 11/2010 |
| WO | 2011/014496 A1 | 2/2011 |
| WO | 2011/037891 A2 | 3/2011 |
| WO | 2011/051942 A1 | 5/2011 |
| WO | 2011/089601 A1 | 7/2011 |

(56) References Cited

FOREIGN PATENT DOCUMENTS

| WO | 2011/097355 A2 | 8/2011 |
|---|---|---|
| WO | 2011/143263 A2 | 11/2011 |
| WO | 2011/153408 A1 | 12/2011 |
| WO | 2012/127309 A4 | 9/2012 |
| WO | 2013/003228 A1 | 1/2013 |
| WO | 2013/011502 A2 | 1/2013 |
| WO | 2013/028145 A1 | 2/2013 |
| WO | 2013/179295 A2 | 12/2013 |
| WO | 2014/043527 A2 | 3/2014 |
| WO | 2014/087402 A1 | 6/2014 |
| WO | 2014/018903 A1 | 7/2014 |
| WO | 2014/108903 A1 | 7/2014 |
| WO | 2014/141239 A1 | 9/2014 |
| WO | 2015/015497 A1 | 2/2015 |
| WO | 2015/063580 A2 | 5/2015 |
| WO | 2015/193728 A2 | 12/2015 |
| WO | 2016/011275 A2 | 1/2016 |
| WO | 2016/087934 A1 | 6/2016 |

OTHER PUBLICATIONS

Japanese Office Action translation dated Oct. 28, 2014; Appln. No. 549463/2012.
Shikhar Agarwal, et al; "Interventional Cardiology Perspective of Functional Tricuspid Regurgitation", Circ. Cardiovas. Interv. 2009; vol. 2, pp. 565-573.
Ottavio Alfieri; "An Effective Technique to Correct Anterior Mitral Leaflet Prolapse", J. Card. Surg. 14(6): 468-470; 1999.
Ottavio Alfieri, et al; "The double-orifice technique in mitral valve repair: A simple solution for complex problems", The Journal of Thoracic and Cardiovascular Surgery, 2001; vol. 122: pp. 674-681.
Ottavio Alfieri, et al; "Novel Suture Device for Beating-Heart Mitral Leaflet Approximation", Presented at the Poster Session of the Thirty-Eighth Annual Meeting of the Society of Thoracic Surgeons, Fort Lauderdale, FL, Jan. 28-30, 2002; 8 pages.
Amplatzer Cardiacc Plug Brochure (English Pages), AGA Medical Corporation, Plymouth, MN Copyright 2008-2011, downloaded Jan. 11, 2011, 16 pages.
Brian S. Beale; "Surgical Repair of Collateral Ligament Injuries", Presented at 63rd CVMA Convention, Halifax, Nova Scotia, Canada, Jul. 6-9, 2011; 4 pages.
Dentistry Today: "Implant Direct", product information page, Jun. 1, 2011, downloaded Dec. 10, 2012 from http://dentistrytoday.com/top25implanti/5558-implant-direct.
Francesco Maisano, et al; "The double-orifice technique as a standardized approach to treat mitral regurgitation due to severe myxomatous disease: surgical technique", European Journal of Cardio-thoracic Surgery, 17, pp. 201-205, 2000.
Smith & Nephew MINITAC™ TI2.0 Suture Anchor Product Description, downloaded on Dec. 9, 2012 from http://global.smith-nephew.com/us/MINITAC_TI_2_SUTURE_ANCHR_3127.htm.
U.S. Appl. No. 60/902,146, filed Feb. 16, 2007.
U.S. Appl. No. 61/897,491, filed Oct. 30, 2013.
USPTO NFOA dated Jul. 6, 2012 in connection with U.S. Appl. No. 12/692,061.
USPTO Interview Summary dated Nov. 5, 2012 in connection with U.S. Appl. No. 12/692,061.
USPTO NOA dated Mar. 6, 2013 in connection with U.S. Appl. No. 12/692,061.
USPTO NOA dated May 10, 2013 in connection with U.S. Appl. No. 12/692,061.
USPTO NOA dated Dec. 4, 2014 in connection with U.S. Appl. No. 13/188,175.
USPTO NFOA dated Dec. 5, 2013 in connection with U.S. Appl. No. 13/485,145.
USPTO FOA dated Jul. 7, 2014 in connection with U.S. Appl. No. 13/485,145.
USPTO FOA dated Sep. 25, 2014 in connection with U.S. Appl. No. 13/485,145.
USPTO NOA dated Dec. 9, 2014 in connection with U.S. Appl. No. 13/485,145.
USPTO NFOA dated Nov. 25, 2014 in connection with U.S. Appl. No. 13/553,081.
USPTO Summary dated Feb. 2, 2015 in connection with U.S. Appl. No. 14/143,355.
Invitation to Pay Additional Fees dated Apr. 4, 2014; PCT/IL2014/05002.
International Search Report and Written Opinion dated May 19, 2011; PCT/IL11/00064.
international Search Report and Written Opinion dated Jan. 22, 2013; PCT/IL2012/000282.
International Search Report and Written Opinion dated Mar. 17, 2014; PCT/IL13/50937.
International Search Report and Written Opinion dated Dec. 6, 2013; PCT/IL2013/050470.
International Search Report and Written Opinion dated May 28, 2014; PCT/IL2014/050027.
International Search Report and Written Opinion dated Jun. 30, 2014; PCT/IL2014/050233.
Invitation to Pay Additional Fees; dated Oct. 13, 2016; PCT/IB2016/000840.
USPTO NFOA dated Sep. 14, 2016 in connection with U.S. Appl. No. 13/574,088.
USPTO Interview Summary dated Dec. 5, 2016 in connection with U.S. Appl. No. 13/574,088.
Extended European Search Report dated Apr. 10, 2015; Appln. No./Patent No. 11734451.5-1662/2525741 PCT/IL2011000064.
Extended European Search Report dated May 15, 2015; Appln. No./Patent No. 12814417.7-1506/2734157 PCT/IL2012000282.
Invitation to Pay Additional Fees; dated Apr. 20, 2015; PCT/IB2014/002351.
International Search Report and Written Opinion dated Jun. 10, 2015; PCT/IB2014/002351.
Japanese Office Action dated Jul. 7, 2015; Application No. 549463/2012.
Second Chinese Office Action dated Feb. 10, 2015; Appln. No. 201180015301.6.
Third Chinese Office Action dated Jun. 30, 2015; Appln. No. 201180015301.6.
USPTO NOA dated Sep. 14, 2015 in connection with U.S. Appl. No. 13/553,081.
USPTO RR dated Feb. 25, 2015 in connection with U.S. Appl. No. 13/574,088.
USPTO NFOA dated Oct. 7, 2015 in connection with U.S. Appl. No. 13/754,088.
Invitation to Pay Additional Fees; dated Oct. 26, 2015; PCT/IB15/01196.

\* cited by examiner

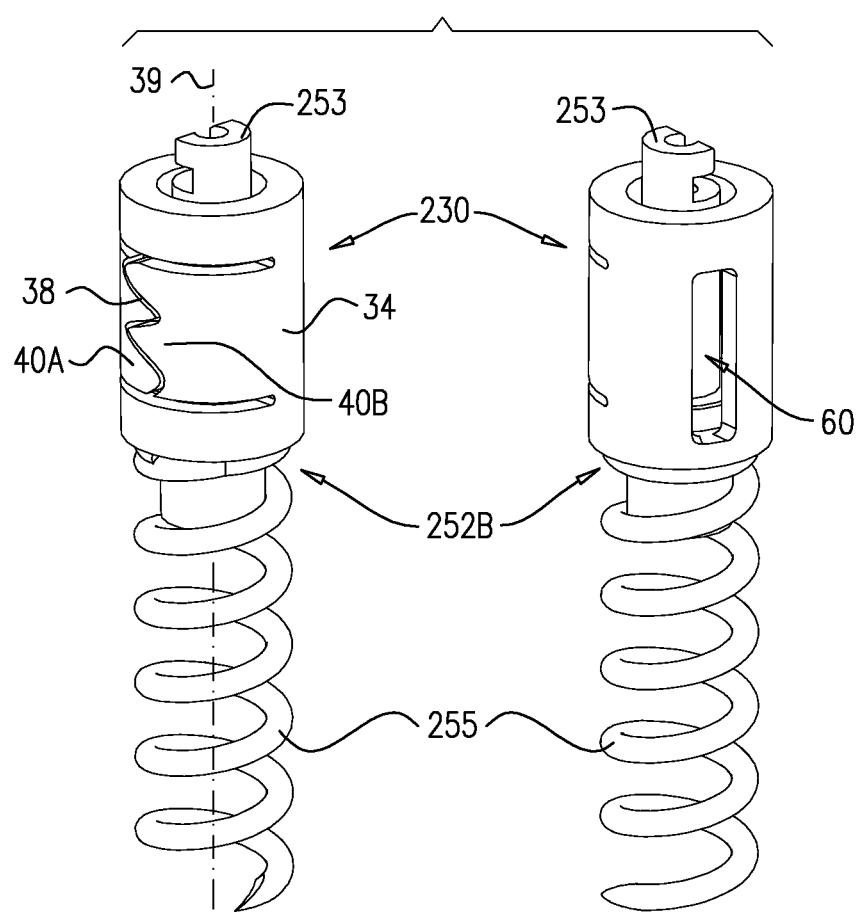

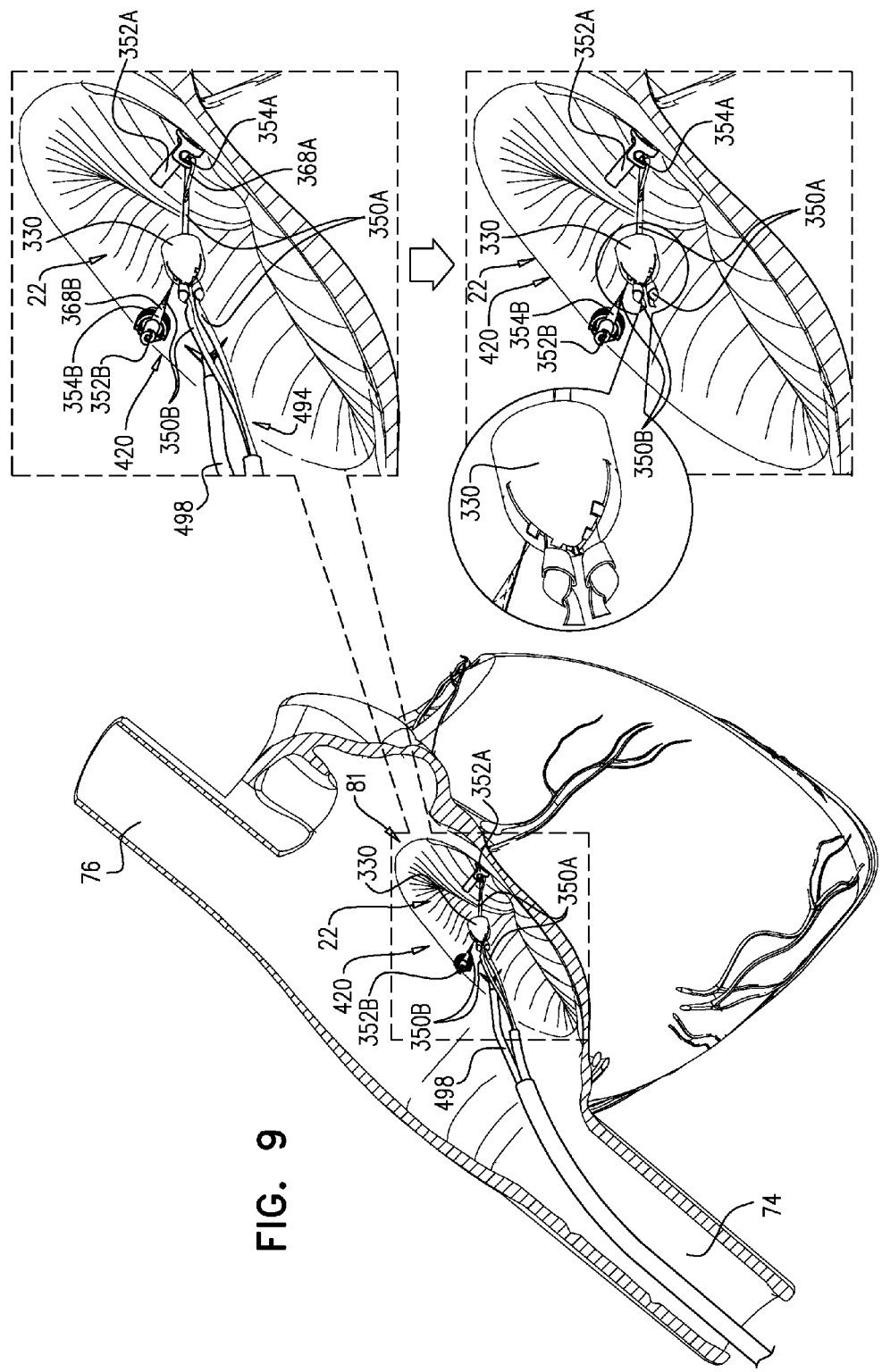

ial Application 61/897,491, filed Oct. 30, 2013, which is
PERCUTANEOUS TETHER LOCKING

CROSS-REFERENCE TO RELATED APPLICATIONS

The present application claims priority from U.S. Provisional Application 61/897,491, filed Oct. 30, 2013, which is assigned to the assignee of the present application and is incorporated herein by reference.

FIELD OF THE APPLICATION

Some applications of the present invention relate in general to valve repair. More specifically, some applications of the present invention relate to repair of an atrioventricular valve of a patient.

BACKGROUND OF THE APPLICATION

Functional tricuspid regurgitation (FTR) is governed by several pathophysiologic abnormalities such as tricuspid valve annular dilatation, annular shape abnormality, pulmonary hypertension, left or right ventricle dysfunction, right ventricle geometry, and leaflet tethering. Treatment options for FTR are primarily surgical. The current prevalence of moderate-to-severe tricuspid regurgitation is estimated to be 1.6 million in the United States. Of these, only 8,000 patients undergo tricuspid valve surgeries annually, most of them in conjunction with left heart valve surgeries.

SUMMARY OF APPLICATIONS

Some embodiments of the present invention provide techniques for tightening tethers of percutaneous implants transluminally, in order to enable percutaneous treatment of functional tricuspid regurgitation (FTR). In some applications of the invention, techniques are provided for fixing two or more tethers to each other, or two portions of a single tether to one another, in order to apply and maintain tension between two or more tissue anchors implanted in tissue of a subject.

In some applications of the present invention, a tether-securing device comprises a serrated tubular element that allows passage of one or more tethers or longitudinal portions of tethers band in one direction, but inhibits (e.g., prevents) the return of the tether(s) in the opposite direction.

In other applications of the present invention, a tether-securing device is configured to assume an unlocked configuration, in which one or more tethers are generally slidable through the device, and a one-way-locked configuration, in which the tether(s) are slidable only in one direction through the device. For some applications, the tether-securing device is configured to be biased to assume the one-way-locked configuration thereof, and is retained in the unlocked configuration by a constraint. For such applications, the devices automatically transition to the one-way-locked configuration when the constraint is removed.

In some applications of the present invention, excess portions of the tether(s) are cut off proximal to the tether-securing device after it is locked in place. For such applications, a delivery system for implanting the implant also comprises a tool for shearing off and retrieving the excess material, such as thoracoscopic scissors, as known in the art.

In other applications of the present invention, excess portions of the tether(s) are held in place by a fixation device such as a stent, which is placed in the vasculature leading to the atrium, such as the superior vena cava (SVC), the inferior vena cava (IVC), or the coronary sinus (CS). For such applications, the delivery system is configured to connect the excess material to the fixation device.

In some applications of the present invention, techniques are provided for using tether-securing devices to repair a heart valve, by fixedly coupling together textile bands that are coupled to different parts of an annulus of a heart valve.

There is therefore provided, in accordance with an application of the present invention, apparatus including:

at least one tether, having first and second tether end portions;

first and second tissue anchors, fixed to the first and the second tether end portions, respectively; and a tether-securing device, which includes:

a tubular element, which is shaped so as define a lumen through which the at least one tether passes, and has proximal and distal tube ends; and three or more locking pieces, which extend proximally from the proximal end of the tubular element, wherein the tether-securing device is configured:

to assume an unlocked configuration when the locking pieces are in a constrained state, in which the locking pieces extend proximally and allow distal and proximal sliding of the at least one tether through the lumen, and to assume a one-way-locked configuration when the locking pieces are in a relaxed state, in which the locking pieces extend proximally and radially inward toward one another and inhibit the distal sliding more than when in the constrained state.

For some applications, the locking pieces are configured to allow the proximal sliding when in the relaxed state.

For some applications, the locking pieces are convex, as viewed from outside the tether-securing device, at least when the locking pieces are in the relaxed state.

For some applications, the tubular element is cylindrical.

For some applications, the locking pieces are integral with the tubular element.

For some applications, the three or more locking pieces include exactly three locking pieces or exactly four locking pieces.

For some applications, the lumen is a securing-device lumen, and the apparatus further includes a delivery tool, which includes a catheter shaft, which (a) is configured to apply a constraining force to the locking pieces when the shaft is disposed in the securing-device lumen, which constraining force retains the tether-securing device in the unlocked configuration, and (b) is shaped so as to define a shaft lumen, through which the at least one tether removably slidably passes.

For some applications, a total axial length of the tether-securing device, when the locking pieces are in the relaxed state, is between 3 and 50 mm.

For any of the applications described above, each of the locking pieces may be shaped so as to define two curved edges that meet at a proximal tip. For some applications, the proximal edges are shaped so as to define uneven edge surfaces. For some applications, the uneven edge surfaces are shaped so as define teeth. For some applications, the uneven edge surfaces are rough.

For any of the applications described above, the at least one tether defines a plurality of securement protrusions spaced at intervals along the at least one tether. For some applications, the protrusions are defined by respective knots in the at least one tether. For some applications, the protrusions include respective elements selected from the group consisting of: cones, scales, and beads. For some applications, an average interval of the securement protrusions is between 1 and 5 mm.

For any of the applications described above, the at least one tether may include first and second tethers, which have the first and the second tether end portions, respectively.

For any of the applications described above, a single tether of the at least one tether may have the first and the second tether end portions, and the single tether may include at least the following non-overlapping longitudinal portions disposed in sequence along the single tether:
 the first tether end portion,
 a first portion that passes through the lumen,
 a looped middle portion that extends out of and away from the lumen, and then loops back to the lumen,
 a second portion that passes through the lumen, and
 the second tether end portion.

For some applications, the apparatus further includes a fixation tether, which is connected to the looped middle portion of the single tether. For some applications, the apparatus further includes a venous tissue anchor, which is configured to be implanted in a vein selected from the group of veins consisting of: an inferior vena cava, a superior vena cava, and a coronary sinus, and which is connected to the fixation tether. For some applications, the venous tissue anchor includes a stent.

For any of the applications described above, the apparatus further includes:
 a venous tissue anchor, which is configured to be implanted in a vein selected from the group of veins consisting of: an inferior vena cava, a superior vena cava, and a coronary sinus; and
 a fixation tether, which is connected to the venous tissue anchor and the at least one tether.

For some applications, the venous tissue anchor includes a stent.

There is further provided, in accordance with an application of the present invention, apparatus including:
 a tether-securing device, which includes a tubular element, which is shaped so as define a lateral wall that surrounds a lumen, wherein the lateral wall is shaped so as to define a one-way locking opening;
 at least one tether, which (a) has at least a first tether end portion, and (b) passes through the lumen and the one-way locking opening; and
 first and second tissue anchors, wherein the first tissue anchor is connected to the first tether end portion,
 wherein the one-way locking opening is configured to (a) allow sliding of the at least one tether in a first direction through the one-way locking opening, and (b) inhibit sliding of the at least one tether in a second direction opposite the first direction.

For some applications, the one-way locking opening is shaped as a slit.

For some applications, the first direction is from inside the tubular element to outside the tubular element.

For some applications, the tubular element is cylindrical.

For some applications, an axial length of the tubular element is between 5 and 20 mm.

For any of the applications described above, the one-way locking opening may have uneven edges. For some applications, the uneven edges are jagged or serrated.

For any of the applications described above, the at least one tether may define a plurality of securement protrusions spaced at intervals along the at least one tether. For some applications, the protrusions are defined by respective knots in the at least one tether. For some applications, the protrusions include respective elements selected from the group consisting of: cones, scales, and beads. For some applications, an average interval of the securement protrusions is between 1 and 5 mm.

For any of the applications described above, a single tether of the at least one tether may have the first tether end portion and a second tether end portion, which second tether end portion is connected to the second tissue anchor, and the single tether may include at least the following non-overlapping longitudinal portions disposed in sequence along the single tether:
 the first tether end portion,
 a first portion that passes through the securing-device lumen and the one-way locking opening,
 a looped middle portion that extends out of and away from the one-way locking opening, and then loops back to the one-way locking opening,
 a second portion that passes through the securing-device lumen and the one-way locking opening, and
 the second tether end portion.

For some applications, the lateral wall is shaped so as to define first and second non-constraining openings, which are sized and shaped to allow free sliding therethrough of two longitudinal portions, respectively, of the single tether. For some applications, the non-constraining openings are shaped as respective slits. For some applications, the apparatus further includes a fixation tether, which is connected to the looped middle portion of the single tether. For some applications, the apparatus further includes a venous tissue anchor, which is configured to be implanted in a vein selected from the group of veins consisting of: an inferior vena cava, a superior vena cava, and a coronary sinus, and which is connected to the fixation tether. For some applications, the venous tissue anchor includes a stent.

For any of the applications described above, the second tissue anchor may include a head and a tissue-coupling element, and the tether-securing device is fixed to the head, such that the tether-securing device surrounds at least a portion of the head. For some applications, the tether-securing device is configured to rotate with respect to the head. For some applications, the lateral wall is shaped so as to define a non-constraining opening, which is sized and shaped to allow free sliding therethrough of the at least one tether. For some applications, the non-constraining opening is shaped as a slit.

For any of the applications described above:
 the at least one tether may include first and second tethers, which (a) have the first tether end portion and a second tether end portion, respectively, and (b) pass through (i) the lumen and (ii) the one-way locking opening,
 the second tissue anchor may be connected to the second tether end portion, and
 the one-way locking opening may be configured to (a) allow the sliding of the first and the second tethers in the first direction through the one-way locking opening, and (b) inhibit the sliding of the first and the second tethers in the second direction.

For some applications, the lateral wall is shaped so as to define first and second non-constraining openings, which are sized and shaped to allow free sliding therethrough of the first and the second tethers, respectively. For some applications, the non-constraining openings are shaped as respective slits.

For any of the applications described above, the apparatus may further include:

a venous tissue anchor, which is configured to be implanted in a vein selected from the group of veins consisting of: an inferior vena cava, a superior vena cava, and a coronary sinus; and a fixation tether, which is connected to the venous tissue anchor and the at least one tether.

For some applications, the venous tissue anchor includes a stent.

There is still further provided, in accordance with an application of the present invention, apparatus including:

a tether, having first and second tether end portions;

first and second tissue anchors, fixed to the first and the second tether end portions, respectively; and a tether-securing device, the tether includes at least the following non-overlapping longitudinal portions disposed in sequence along the tether:

the first tether end portion, a first portion that passes through the lumen, a looped middle portion that (a) extends out of and away from the tether-securing device and (b) then loops back to the tether-securing device, a second portion that passes through the tether-securing device, and the second tether end portion.

For some applications, the looped middle portion extends out of and away from the tether-securing device such that a longitudinal center of the looped middle portion is not in direct physical contact with any portion of the tether-securing device.

For some applications, the tether-securing device is configured to assume:

an unlocked configuration, in which the tether-securing device allows distal and proximal sliding of the first and the second portions of the tether therethrough, and a one-way-locked configuration, in which the tether-securing device inhibits the distal sliding more than when in the unlocked configuration.

For some applications, the tether-securing device is configured to assume:

an unlocked configuration, in which the tether-securing device allows distal and proximal sliding of the first and the second portions of the tether therethrough, and a locked configuration, in which the tether-securing device inhibits the distal and proximal sliding.

For some applications, the tether-securing device is configured to (a) allow sliding of the first and the second portions of the tether in a first direction through the tether-securing device, and (b) inhibit sliding of the first and the second portions of the tether in a second direction opposite the first direction.

For any of the applications described above, the apparatus may further include a fixation tether, which is connected to the looped middle portion of the tether. For some applications, the apparatus further includes a venous tissue anchor, which is configured to be implanted in a vein selected from the group of veins consisting of: an inferior vena cava, a superior vena cava, and a coronary sinus, and which is connected to the fixation tether. For some applications, the venous tissue anchor includes a stent.

There is additionally provided, in accordance with an application of the present invention, apparatus including:

an implant, which includes:

at least first and second tissue anchors, which include (a) first and second helical tissue coupling elements, respectively, and (b) first and second heads, respectively, which include first and second tether interfaces; and a tether, which is connected to the first tether interface, and coupled to the second tether interface; and a multiple-anchor delivery tool, which includes:

a catheter shaft having proximal and distal ends, wherein the first and the second tissue anchors are removably positioned in the catheter shaft at first and second longitudinal locations, respectively, the first longitudinal location more distal than the second longitudinal location; and first and second torque cables, which (a) are removably coupled to the first and the second heads, respectively, (b) extend within the catheter shaft proximally from the first and the second heads, respectively, and (c) transmit torque when rotated, wherein a portion of the first torque cable is removably positioned alongside the second tissue anchor in the catheter shaft.

For some applications:

the implant further includes a third tissue anchor, which includes (a) a third helical tissue coupling elements and (b) a third head, which includes a third tether interface, the tether, which is coupled to the third tether interface, the third tissue anchor is removably positioned in the catheter shaft at a third longitudinal location that is more proximal than the second longitudinal location, and the multiple-anchor delivery tool further includes a third torque cable, which (a) is removably coupled to the third head, (b) extends within the catheter shaft proximally from the third head, and (c) transmits torque when rotated, and a portion of the second torque cable is removably positioned alongside the third tissue anchor in the catheter shaft.

For some applications, the first tether interface is rotatable with respect to the first tissue-coupling element.

For any of the applications described above, the first torque cable may be shaped so as to define a lumen therethrough, and the multiple-anchor delivery tool may further include a shaft, which removably passes through the lumen.

For some applications:

the head is shaped so as to define a proximal coupling element, the head, including the proximal coupling element, is shaped so as to define a first longitudinal channel at least partially therethrough, which channel is coaxial with the head, a distal end of the first torque cable includes a distal coupling element, which is shaped so as to define a second longitudinal channel therethrough, which channel is coaxial with the lumen of the first torque cable, the proximal and the distal coupling elements are shaped so as to define corresponding interlocking surfaces, and the shaft, when disposed through the first and the second channels, prevents decoupling of the distal coupling element from the proximal coupling element.

For some applications, the shaft is shaped so as to define a sharp distal tip.

There is yet additionally provided, in accordance with an application of the present invention, a method including:

delivering, to a vicinity of an anatomical site of a subject, (a) at least one tether, having first and second tether end portions, (b) first and second tissue anchors, fixed to the first and the second tether end portions, respectively, and (c) a tether-securing device, which includes (i) a tubular element, which is shaped so as define a lumen through which the at least one tether passes, and has proximal and distal tube ends, and (ii) three or more locking pieces, which extend proximally from the proximal end of the tubular element;

implanting the first and the second tissue anchors in tissue of the subject;

tensioning the at least one tether by proximally sliding the at least one tether through the lumen while the tether-securing device is in an unlocked configuration in which the locking pieces are in a constrained state, in which state the locking pieces extend proximally and allow distal and proximal sliding of the at least one tether through the lumen; and transitioning the tether-securing device to a one-way-locked configuration in which the locking pieces are in a relaxed state, in which state the locking pieces extend proximally and radially inward toward one another and inhibit the distal sliding more than when in the constrained state.

For some applications, the locking pieces are configured to allow proximal sliding when in the relaxed state, and tensioning includes further tensioning the at least one tether by further proximally sliding the at least one tether through the lumen after transitioning the tether-securing device to the one-way-locked configuration.

For some applications:
a single tether of the at least one tether has the first and the second tether end portions,
the single tether includes at least the following non-overlapping longitudinal portions disposed in sequence along the single tether:
the first tether end portion,
a first portion that passes through the lumen,
a looped middle portion that extends out of and away from the lumen, and then loops back to the lumen,
a second portion that passes through the lumen, and
the second tether end portion, and
tensioning the tether includes proximally sliding the first and the second portions of the tether through the lumen by pulling on the looped middle portion.

For some applications, the method further includes connecting a fixation tether to the looped middle portion of the single tether.

For some applications, the method further includes implanting a venous tissue anchor, which is connected to the fixation tether, in a vein selected from the group of veins consisting of: an inferior vena cava, a superior vena cava, and a coronary sinus.

For some applications, implanting the venous tissue anchor includes implanting a stent.

For some applications, the at least one tether includes first and second tethers, which have the first and the second tether end portions, respectively, and tensioning the at least one tether includes tensioning the first and the second tethers by proximally sliding the first and the second tethers through the lumen.

For some applications, each of the locking pieces is shaped so as to define two curved edges that meet at a proximal tip. For some applications, the proximal edges are shaped so as to define uneven edge surfaces. For some applications, the uneven edge surfaces are shaped so as define teeth. For some applications, the uneven edge surfaces are rough.

For some applications, the locking pieces are convex, as viewed from outside the tether-securing device, at least when the locking pieces are in the relaxed state.

For some applications, the at least one tether defines a plurality of securement protrusions spaced at intervals along the at least one tether. For some applications, the protrusions are defined by respective knots in the at least one tether. For some applications, the protrusions include respective elements selected from the group consisting of: cones, scales, and beads. For some applications, an average interval of the securement protrusions is between 1 and 5 mm.

For some applications, a total axial length of the tether-securing device, when the locking pieces are in the relaxed state, is between 10 and 50 mm.

For some applications, the tubular element is cylindrical.
For some applications, the locking pieces are integral with the tubular element.

For some applications, the three or more locking pieces include exactly three locking pieces or exactly four locking pieces.

For some applications:
the lumen is a securing-device lumen,
delivering the at least one tether and the tether-securing device includes delivering the at least one tether and the tether-securing device using a delivery tool, which includes a catheter shaft, which (a) applies a constraining force to the locking pieces when the shaft is disposed in the securing-device lumen, which constraining force retains the tether-securing device in the unlocked configuration, and (b) is shaped so as to define a shaft lumen, through which the at least one tether removably slidably passes, and
transitioning the tether-securing device to a one-way-locked configuration includes removing the catheter shaft from the securing-device lumen.

For some applications, the method further includes:
implanting a venous tissue anchor in a vein selected from the group of veins consisting of: an inferior vena cava, a superior vena cava, and a coronary sinus; and
connecting, to the at least one tether, a fixation tether which is connected to the venous tissue anchor.

For some applications, implanting the venous tissue anchor includes implanting a stent.

There is also provided, in accordance with an application of the present invention, a method including:
delivering, to a vicinity of an anatomical site of a subject:
(a) a tether-securing device, which includes a tubular element, which is shaped so as define a lateral wall that surrounds a lumen, wherein the lateral wall is shaped so as to define a one-way locking opening, which is configured to (i) allow sliding of the at least one tether in a first direction through the one-way locking opening, and (ii) inhibit sliding of the at least one tether in a second direction opposite the first direction,
(b) at least one tether, which (i) has at least a first tether end portion, and (ii) passes through the lumen and the one-way locking opening, and
(c) first and second tissue anchors, wherein the first tissue anchor is connected to the first tether end portion;
implanting the first and the second tissue anchors in tissue of the subject; and
tensioning the at least one tether by sliding the at least one tether in the first direction through the one-way locking opening.

For some applications, a single tether of the at least one tether has the first tether end portion and a second tether end portion, which second tether end portion is connected to the second tissue anchor, and the single tether includes at least the following non-overlapping longitudinal portions disposed in sequence along the single tether:
the first tether end portion,
a first portion that passes through the securing-device lumen and the one-way locking opening,
a looped middle portion that extends out of and away from the one-way locking opening, and then loops back to the one-way locking opening, a second portion that passes through the securing-device lumen and the one-way locking opening, and the second tether end portion, and tensioning the tether includes proximally sliding the first and the second portions of the tether through the one-way locking opening in the first direction by pulling, in the first direction, on the looped middle portion.

For some applications:

the lateral wall is shaped so as to define first and second non-constraining openings, which are sized and shaped to allow free sliding therethrough of two longitudinal portions, respectively, of the single tether, and sliding the tether through the one-way locking opening further includes sliding the two non-overlapping longitudinal portions of the tether through the first and the second non-constraining openings, respectively.

For some applications, the non-constraining openings are shaped as respective slits. For some applications, the method further includes connecting a fixation tether to the looped middle portion of the single tether. For some applications, the method further includes implanting a venous tissue anchor, which is connected to the fixation tether, in a vein selected from the group of veins consisting of: an inferior vena cava, a superior vena cava, and a coronary sinus. For some applications, implanting the venous tissue anchor includes implanting a stent.

For some applications, the second tissue anchor includes a head and a tissue-coupling element, and the tether-securing device is fixed to the head, such that the tether-securing device surrounds at least a portion of the head. For some applications, the tether-securing device is configured to rotate with respect to the head.

For some applications, the lateral wall is shaped so as to define a non-constraining opening, which is sized and shaped to allow free sliding therethrough of the tether, and sliding the tether through the one-way locking opening further includes sliding the tether through the non-constraining opening.

For some applications, the non-constraining opening is shaped as a slit.

For some applications:

the at least one tether includes first and second tethers, which (a) have the first tether end portion and a second tether end portion, respectively, and (b) pass through (i) the lumen and (ii) the one-way locking opening, the second tissue anchor is connected to the second tether end portion, the one-way locking opening is configured to (a) allow the sliding of the first and the second tethers in the first direction through the one-way locking opening, and (b) inhibit the sliding of the first and the second tethers in the second direction, and tensioning the at least one tether includes tensioning the first and the second tethers by sliding the first and the second tethers in the first direction through the one-way locking opening.

For some applications:

the lateral wall is shaped so as to define first and second non-constraining openings, which are sized and shaped to allow free sliding therethrough of the first and the second tethers, respectively, the first and the second tethers slidably pass through the first and the second non-constraining openings, respectively, and sliding the first and the second tethers through the one-way locking opening further includes sliding the first and the second tethers through the first and the second non-constraining openings, respectively.

For some applications, the non-constraining openings are shaped as respective slits.

For some applications, the one-way locking opening is shaped as a slit.

For some applications, the first direction is from inside the tubular element to outside the tubular element.

For some applications, the one-way locking opening has uneven edges. For some applications, the uneven edges are jagged or serrated.

For some applications, an axial length of the tubular element is between 5 and 20 mm.

For some applications, the tubular element is cylindrical.

For some applications, the at least one tether defines a plurality of securement protrusions spaced at intervals along the at least one tether. For some applications, the protrusions are defined by respective knots in the at least one tether. For some applications, the protrusions include respective elements selected from the group consisting of: cones, scales, and beads.

For some applications, an average interval of the securement protrusions is between 1 and 5 mm.

For some applications, the method further includes:

implanting a venous tissue anchor in a vein selected from the group of veins consisting of: an inferior vena cava, a superior vena cava, and a coronary sinus; and connecting, to the at least one tether, a fixation tether which is connected to the venous tissue anchor.

For some applications, implanting the venous tissue anchor includes implanting a stent.

There is further provided, in accordance with an application of the present invention, a method including:

delivering, to a vicinity of an anatomical site of a subject, (a) a tether, having first and second tether end portions, (b) first and second tissue anchors, fixed to the first and the second tether end portions, respectively, and (c) a tether-securing device, wherein the tether includes at least the following non-overlapping longitudinal portions disposed in sequence along the tether: (i) the first tether end portion, (ii) a first portion that passes through the lumen, (iii) a looped middle portion that (1) extends out of and away from the tether-securing device and (2) then loops back to the tether-securing device, (iv) a second portion that passes through the tether-securing device, and (v) the second tether end portion;

implanting the first and the second tissue anchors in tissue of the subject; and tensioning the tether by proximally sliding the first and the second portions of the tether through the tether-securing device by pulling on the looped middle portion.

For some applications, delivering the tether includes delivering the tether such that the looped middle portion extends out of and away from the tether-securing device, such that a longitudinal center of the looped middle portion is not in direct physical contact with any portion of the tether-securing device.

For some applications, the method further includes connecting a fixation tether to the looped middle portion of the tether. For some applications, the method further includes implanting a venous tissue anchor, which is connected to the fixation tether, in a vein selected from the group of veins consisting of: an inferior vena cava, a superior vena cava, and a coronary sinus. For some applications, implanting the venous tissue anchor includes implanting a stent.

For some applications, the tether-securing device is configured to assume:

an unlocked configuration, in which the tether-securing device allows distal and proximal sliding of the first and the second portions of the tether therethrough, and a one-way-locked configuration, in which the tether-securing device inhibits the distal sliding more than when in the unlocked configuration.

For some applications, the tether-securing device is configured to assume:

an unlocked configuration, in which the tether-securing device allows distal and proximal sliding of the first and the second portions of the tether therethrough, and a locked configuration, in which the tether-securing device inhibits the distal and proximal sliding.

For some applications, the tether-securing device is configured to (a) allow sliding of the first and the second portions of the tether in a first direction through the tether-securing device, and (b) inhibit sliding of the first and the second portions of the tether in a second direction opposite the first direction.

There is still further provided, in accordance with an application of the present invention, a method including:

advancing a distal end of a catheter shaft of a multiple-anchor delivery tool into a body of a subject, while (a) first and second tissue anchors are removably positioned in the catheter shaft at first and second longitudinal locations, respectively, the first longitudinal location more distal than the second longitudinal location, wherein the first and the second tissue anchors include (i) first and second helical tissue coupling elements, respectively, and (ii) first and second heads, respectively, which include first and second tether interfaces, and (b) a tether, which is connected to the first tether interface, and is coupled to the second tether interface, is removably positioned in the catheter shaft, wherein the multiple-anchor delivery tool includes first and second torque cables, which (a) are removably coupled to the first and the second heads, respectively, (b) extend within the catheter shaft proximally from the first and the second heads, respectively, and (c) transmit torque when rotated, wherein a portion of the first torque cable is removably positioned alongside the second tissue anchor in the catheter shaft;

implanting the first tissue anchor into tissue of the subject by rotating the first torque cable;

decoupling the first torque cable from the first tissue anchor;

after implanting the first tissue anchor, distally advancing the second tissue anchor in the catheter shaft;

implanting the second tissue anchor into tissue of the subject by rotating the second torque cable; and decoupling the second torque cable from the second tissue anchor.

For some applications:

the first torque cable is shaped so as to define a lumen therethrough, the multiple-anchor delivery tool further includes a sharpened wire, which removably passes through the lumen, and which is initially positioned such that a distal end of the sharpened wire extends distally out of a distal end of the lumen, and the method further includes withdrawing the sharpened wire proximally.

For some applications:

the head is shaped so as to define a proximal coupling element, the head, including the proximal coupling element, is shaped so as to define a first longitudinal channel at least partially therethrough, which channel is coaxial with the head, a distal end of the first torque cable includes a distal coupling element, which is shaped so as to define a second longitudinal channel therethrough, which channel is coaxial with the lumen of the first torque cable, the proximal and the distal coupling elements are shaped so as to define corresponding interlocking surfaces, the sharpened wire, when disposed through the first and the second channels, prevents decoupling of the distal coupling element from the proximal coupling element, and withdrawing the sharpened wire proximally includes decoupling the distal coupling element from the proximal coupling element by withdrawing the sharpened wire proximally.

For some applications, the sharpened wire is shaped so as to define a sharp distal tip. For some applications, implanting the first tissue anchor includes inserting the sharp distal tip of the sharpened wire into the tissue.

For some applications:

advancing includes advancing the distal end of the catheter shaft into the body while (a) a third tissue anchor is removably positioned in the catheter shaft at a third longitudinal location that is more proximal than the second longitudinal location, and the third tissue anchor includes (i) a third helical tissue coupling elements and (ii) a third head, which includes a third tether interfaces, (b) the tether is coupled to the third tether interface, the multiple-anchor delivery tool further includes a third torque cable, which (a) is removably coupled to the third head, (b) extends within the catheter shaft proximally from the third head, and (c) transmits torque when rotated, and a portion of the second torque cable is removably positioned alongside the third tissue anchor in the catheter shaft, and the method further includes:

after implanting the second tissue anchor, distally advancing the third tissue anchor in the catheter shaft;

implanting the third tissue anchor into tissue of the subject by rotating the third torque cable; and decoupling the third torque cable from the third tissue anchor.

For some applications, the first tether interface is rotatable with respect to the first tissue-coupling element.

The present invention will be more fully understood from the following detailed description of applications thereof, taken together with the drawings, in which:

BRIEF DESCRIPTION OF THE DRAWINGS

FIG. 5 is a schematic illustration of a tether-securing device of the implant system of FIGS. 4A-C fixed to second tissue anchor of the implant system, in accordance with an application of the present invention;

FIG. 9 is a schematic illustration of another valve-tensioning implant system, in accordance with an application of the present invention;

DETAILED DESCRIPTION OF APPLICATIONS

Figure 1:
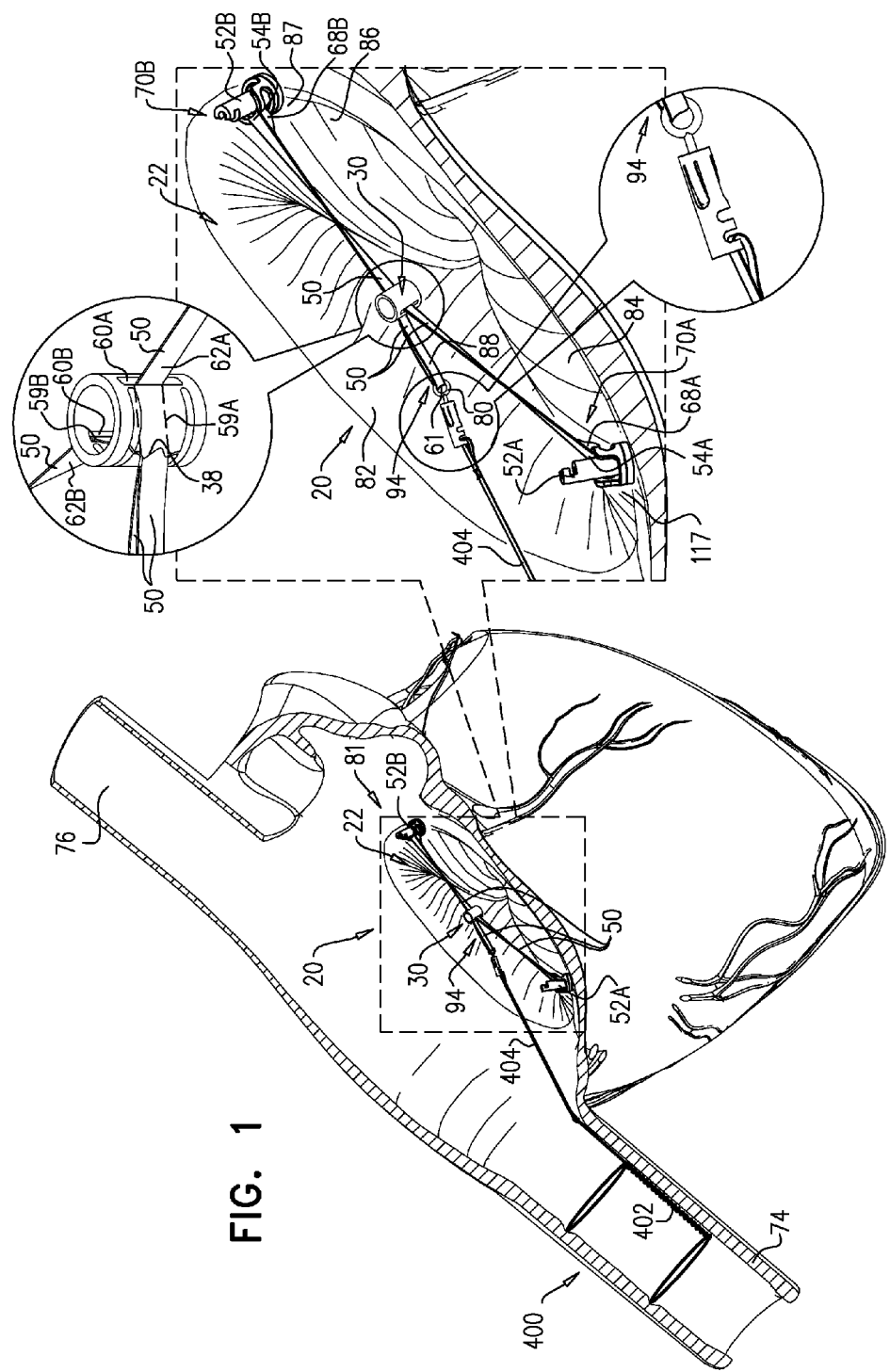
FIG. 1 is a schematic illustration of a valve-tensioning implant system, in accordance with an application of the present invention.

FIG. 1 is a schematic illustration of a valve-tensioning implant system 20, in accordance with an application of the present invention. Valve-tensioning implant system 20 is configured to repair an atrioventricular valve of a subject (e.g., a tricuspid valve 22 or a mitral valve), using tension applied between multiple (e.g., two) anchors of the implant. Typically, repair of the atrioventricular valve facilitates a reduction in atrioventricular valve regurgitation by altering the geometry of the atrioventricular valve and/or by altering the geometry of the wall of the right or left atrium of a heart of the subject. Implant system 20 comprises a tether-securing device 30, at least one tether 50, and first and second tissue anchors 52A and 52B.

For some applications, first and second tissue anchors 52A and 52B are connected (e.g., permanently fixed) to first and second tether end portions 54A and 54B of the at least one tether 50, respectively (typically first and second tissue anchors 52A and 52B are connected to first and second tether ends of the at least one tether 50, respectively). The at least one tether 50 comprises an elongate flexible element, such as a cord, suture, or band. Typically, the at least one tether 50 has a high tensile strength, in order to enable the tether to apply tension, as described hereinbelow. It is noted that, although the tethers described herein are shown as ribbon-shaped sutures (i.e., having a generally rectangular cross-section), any suitable type of textile or suture, as is known in the art, may alternatively be used. For some applications, first and second tether end portions 54A and 54B are configured so as to define anchor-fixing loops 68A and 68B, respectively, which pass through corresponding interfaces on first and second tissue anchors 52A and 52B, respectively, so as to connect (e.g., permanently fix) the tether end portions to the tissue anchors.

Figure 2:
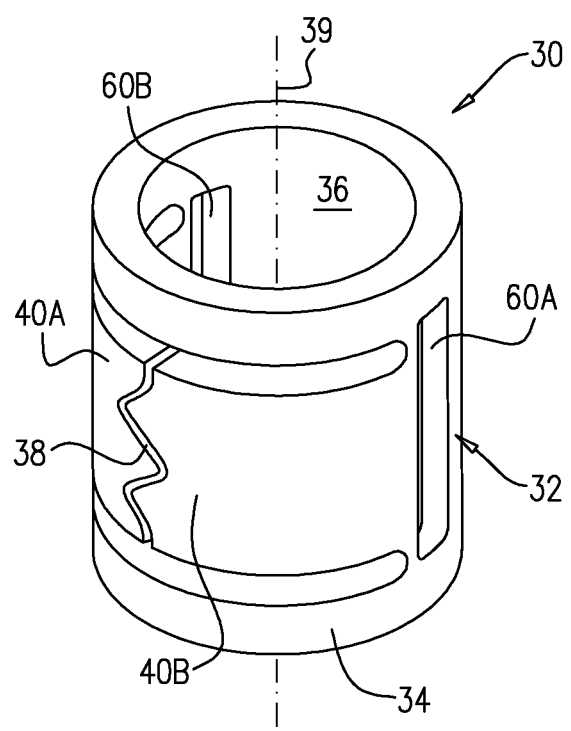
FIG. 2 is a schematic illustration of a tether-securing device of the implant system of FIG. 1, in accordance with an application of the present invention.

Reference is still made to FIG. 1, and is additionally made to FIG. 2, which is a schematic illustration of tether-securing device 30, in accordance with an application of the present invention. Tether-securing device 30 comprises a tubular element 32, which is shaped so as to define a lateral wall 34 that surrounds a securing-device lumen 36. Lateral wall 34 is shaped so as to define a one-way locking opening 38. For some applications, one-way locking opening is shaped as a slit, as shown. For some applications, the slit extends in a direction parallel to a longitudinal axis 39 of tubular element 32. Typically, lateral wall 34 is shaped so as to define at least two pawls 40A and 40B, which together define one-way locking opening 38. Typically, one-way locking opening has uneven edges, which, for example, may be jagged or serrated.

The at least one tether 50 passes through securing-device lumen 36 and one-way locking opening 38. One-way locking opening 38 is configured to (a) allow sliding of the at least one tether 50 in a first direction through one-way locking opening 38, and (b) inhibit (e.g., prevent or limit) sliding of the at least one tether 50 in a second direction opposite the first direction. The one-way locking opening thus allows the tightening of tissue anchors 52A and 52B together, and resists the loosening of the anchors away from one another. For some applications, the first direction is from inside the tubular element to outside the tubular element. For some applications, in order to provide such unidirectional movement of the at least one tether, pawls 40A and 40B are configured to open outwardly but not open inwardly.

For some applications, such as shown in FIG. 1, a single tether 50 of the at least one tether 50 has first and second tether end portions 54A and 54B. (The at least one tether 50 may or may not comprise additional tethers in addition to the single tether.) For these applications, single tether 50 typically comprises at least the following non-overlapping longitudinal portions disposed in sequence along the single tether:

first tether end portion 54A,
    a first portion 59A that passes through securing-device lumen 36 and one-way locking opening 38,
    a looped middle portion 88 that extends out of and away from the one-way locking opening, and then loops back to the one-way locking opening (typically, such that a longitudinal center 61 of looped middle portion 88 is not in direct physical contact with any portion of tether-securing device 30),
    a second portion 59B that passes through securing-device lumen 36 and one-way locking opening 38, and
    second tether end portion 54B.

Typically, the single tether comprises additional longitudinal portions between the above-listed portions, i.e., the above-listed portions are in sequence, but not contiguous with one another. For example, the single tether typically comprises a longitudinal portion between first tether end portion 54A and first portion 59A, and a longitudinal portion between second portion 59B and second tether end portion 54B.

Tether-securing device 30 thus fixes first and second portions 59A and 59B to each other. Typically, the longitudinal location of tether-securing device 30 along the single tether is set during an implantation procedure, such that respective distances between tether-securing device 30 and first and second tissue anchors 52A and 52B are set during the procedure rather than preconfigured. For some applications, these distances are set using echocardiography and by measuring regurgitant flow, annulus dimensions, and/or with the aid of radiopaque markers on tethers between the two tissue anchors. For some applications, the at least one tether 50 comprises exactly one tether 50.

For some applications, lateral wall 34 is shaped so as to define at least one non-constraining opening 60, such as first and second non-constraining openings 60A and 60B, disposed at respective circumferential locations different from the circumferential location of one-way locking opening 38. First and second non-constraining openings 60A and 60B are sized and shaped to allow free sliding therethrough of first and second longitudinal portions 62A and 62B of single tether 50, respectively. Typically, first and second non-overlapping longitudinal portions 62A and 62B slidably pass through first and second non-constraining openings 60A and 60B, respectively. For some applications, non-constraining openings 60 are shaped as respective slits (as shown), circles (not shown), or other shapes. For some applications in which the non-constraining openings are shaped as slits, the slits extend in a direction parallel to longitudinal axis 39 of tubular element 32.

For some applications, as shown, tubular element 32 is cylindrical. Alternatively, the tubular element may have other hollow shapes such as rectangular, triangular, or hexagonal. For some applications, an axial length of tubular element 32 is at least 5 mm, no more than 20 mm, and/or between 5 and 20 mm.

For some applications, first and second tissue anchor 52A and 52B comprise respective atrial tissue anchors. Alternatively or additionally, for some applications, first and second tissue anchor 52A and 52B comprise respective helical tissue-coupling elements, which puncture and screw into cardiac muscle tissue. For some applications, first and second tissue anchor 52A and 52B implement techniques described in U.S. Provisional Application 61/750,427, filed Jan. 9, 2013. Alternatively, each of first and second tissue anchors 52A and 52B comprises a clip, jaws, or a clamp which grips and squeezes a portion of cardiac muscle tissue and does not puncture the cardiac muscle tissue.

Valve-tensioning implant system 20 is typically implanted transvascularly, using a delivery system comprising one or more catheters introduced with the aid of a guidewire, through vasculature of the subject, such as (a) via the femoral vein, through an inferior vena cava 74, and into a right atrium 81, (b) via the basilic vein, through the subclavian vein through a superior vena cava 76, and into right atrium 81, or (c) via the external jugular vein, through the subclavian vein through superior vena cava 76, and into right atrium 81. (Right atrium 81 includes a septal leaflet 82, a posterior leaflet 84, and an anterior leaflet 86.) The procedure is typically performed with the aid of imaging, such as fluoroscopy, transesophageal, transthoracic echocardiography, intravascular ultrasound (IVUS), and/or echocardiography. The procedure may be performed using techniques described in US Patent Application Publication 2012/0035712, which is assigned to the assignee of the present application and is incorporated herein by reference, with reference to FIGS. 1A-D thereof, mutatis mutandis, and/or using techniques described hereinbelow with reference to FIGS. 11-12C.

First and second tissue anchor 52A and 52B are implanted at respective different second atrial sites 70A and 70B, each of which sites is selected from the group of sites consisting of: an annulus of tricuspid valve 22, and a wall of the right atrium of the heart above the annulus. For applications in which first and second tissue anchors 52A and 52B comprise respective helical tissue-coupling elements, the helical tissue-coupling elements are rotated into tissue at the sites, respectively. For example, first and second tissue coupling elements may be implanted within 1 cm of a first site on the annulus and within 1 cm of a second site on the annulus around the valve, respectively. For example, as shown in FIG. 1, first tissue anchor 52A may be implanted within 1 cm of the site on the annulus that circumferentially corresponds to a septoposterior commissure 117 (i.e., is at the same angular location or "o'clock" as the septoposterior commissure), and second tissue anchor 52B may be implanted within 1 cm of a circumferential middle of the annulus 87 along anterior leaflet 86. The pairs of sites are typically diametrically opposed on the annulus of the valve. The direction of the 1 cm from the sites on the annulus described here and hereinbelow may be either circumferentially (i.e., clockwise or counterclockwise) around the annulus, up the wall of right atrium 81 above annulus 83, or a combination of circumferentially around the annulus and up the wall of the atrium.

The size of the tricuspid valve orifice is reduced by tensioning tether 50, so as to reduce regurgitation. Such tensioning may be performed by holding a catheter shaft (such as outer shaft 384, described hereinbelow with reference to FIGS. 6A-C) against a proximal side of tether-securing device 30 while proximally pulling on looped middle portion 88 of tether 50, such that portions of tether 50 are pulled through one-way locking opening 38. For example, a flexible longitudinal guide member 390 (as shown below in FIG. 6C) may be removably coupled to middle portion 88 by a loop 80, such as a ring, using techniques described in US Patent Application Publication 2013/0018459, which is assigned to the assignee of the present application and is incorporated herein by reference, with reference to FIGS. 23-26 thereof, mutatis mutandis (in which flexible longitudinal guide member 2616 corresponds to flexible longitudinal guide member 390 of the present application). Once the tension has been applied, one-way locking opening 38 maintains the tension.

Figure 8A:
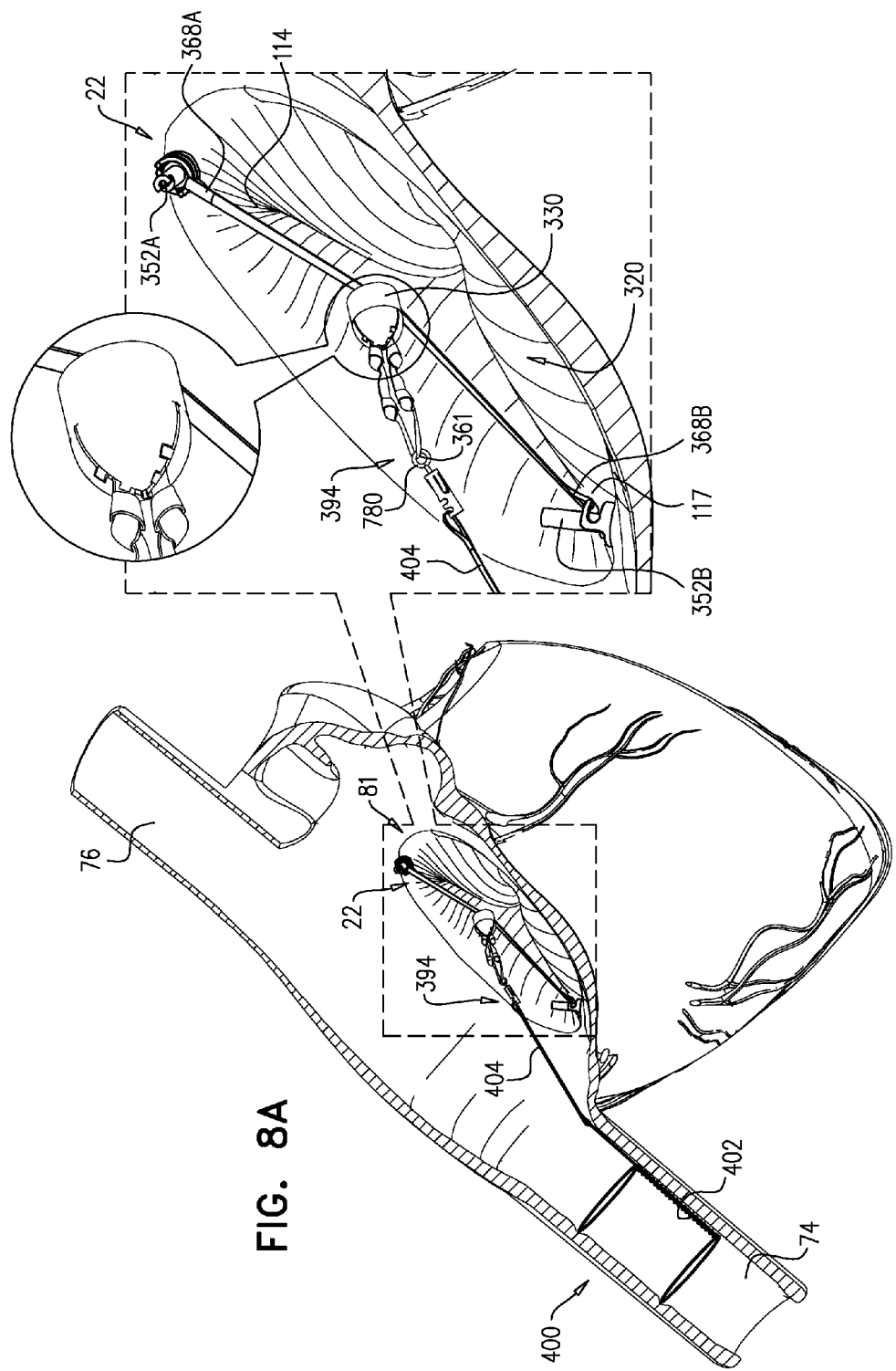
FIGS. 8A-C are schematic illustrations of techniques for securing an excess portion of a tether of the implant system of FIGS. 6A-C and 7A-B, in accordance with respective applications of the present invention.
Figure 8B:
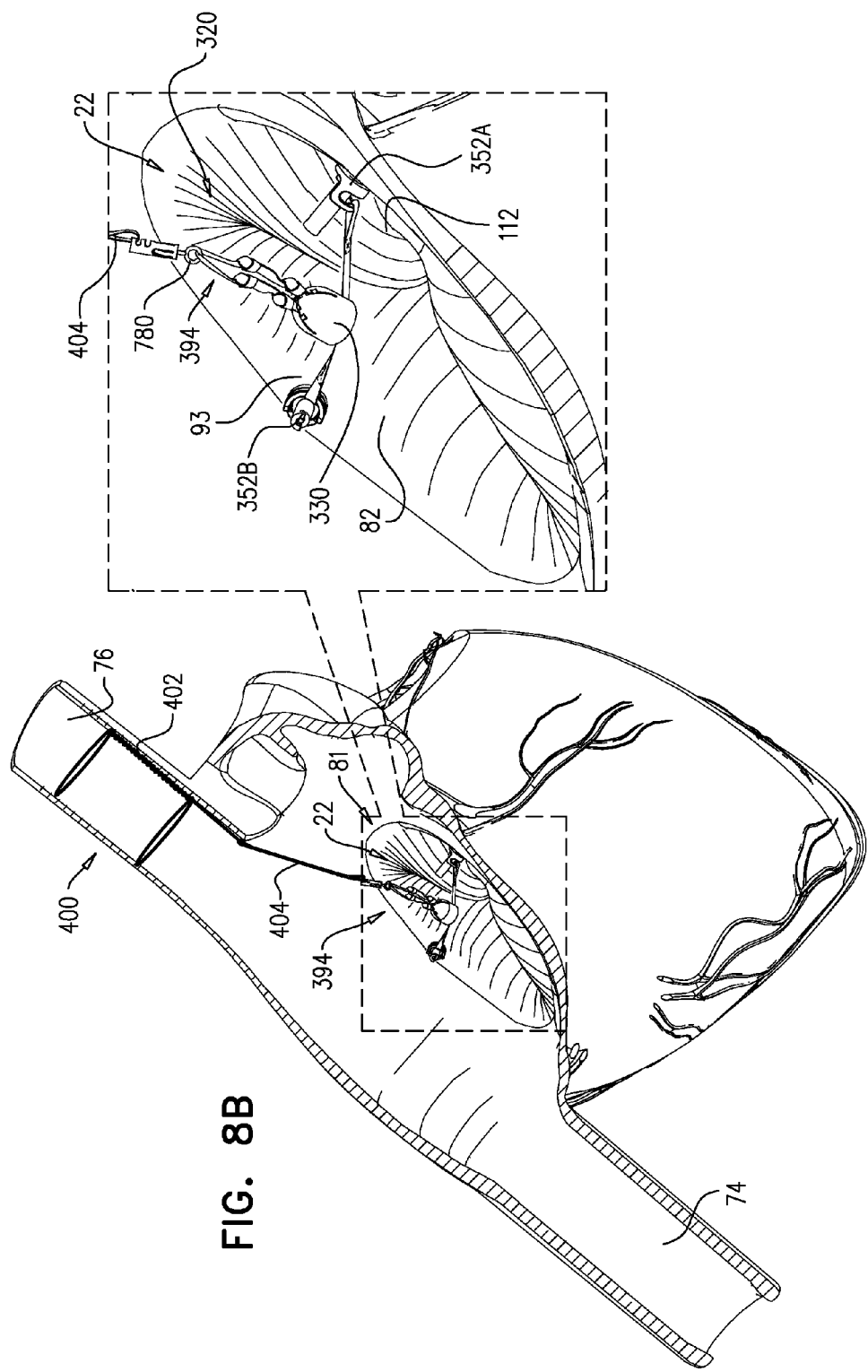
Figure 8C:
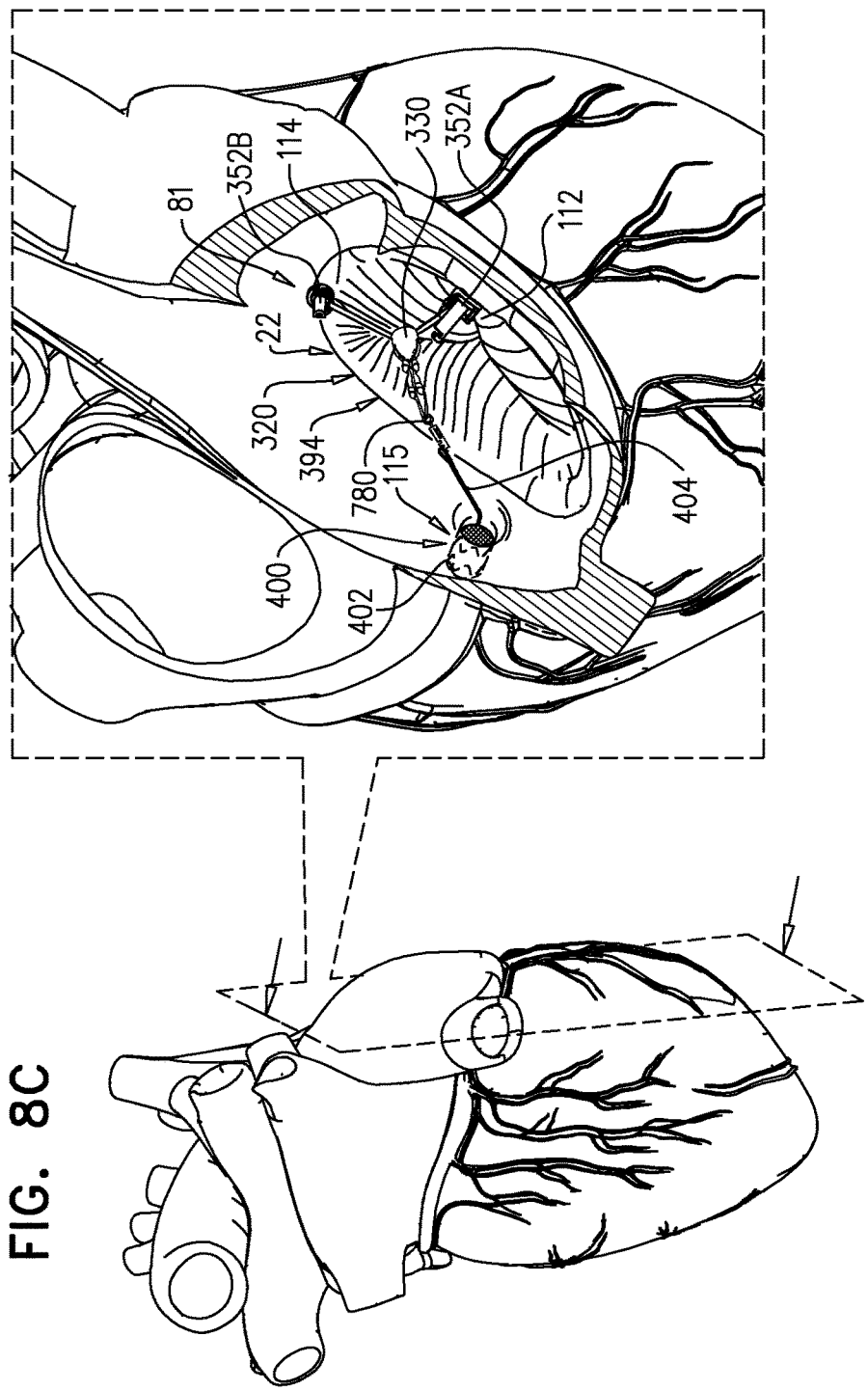

After tether 50 has been tensioned, an excess portion 94 of tether 50 near looped middle portion 88 remains free in right atrium 81. It is generally undesirable to leave this excess portion free to move around in the atrium. For some applications, excess portion is secured in a desired disposition in the vasculature of right atrium 81, such as in inferior vena cava 74 (as shown in FIG. 1), superior vena cava 76 (such as shown in FIG. 8B, mutatis mutandis), or a coronary sinus 115 (such as shown in FIG. 8C, mutatis mutandis). Techniques described hereinbelow with reference to FIGS. 8A-C may be used for such securing, mutatis mutandis. It is noted that in this configuration, venous tissue anchor 400, described hereinbelow with reference to FIGS. 8A-C, is deployed such that only a moderate amount of tension is applied to fixation tether 404, which tension is insufficient to alter the geometry of the atrium annulus and ventricle. Fixation tether 404 is connected, typically during the implantation procedure, to looped middle portion 88, such as by loop 80, e.g., a ring. Alternatively, excess portion 394 is cut and removed from the atrium, such as using techniques described hereinbelow with reference to FIG. 9, mutatis mutandis.

Figure 3:
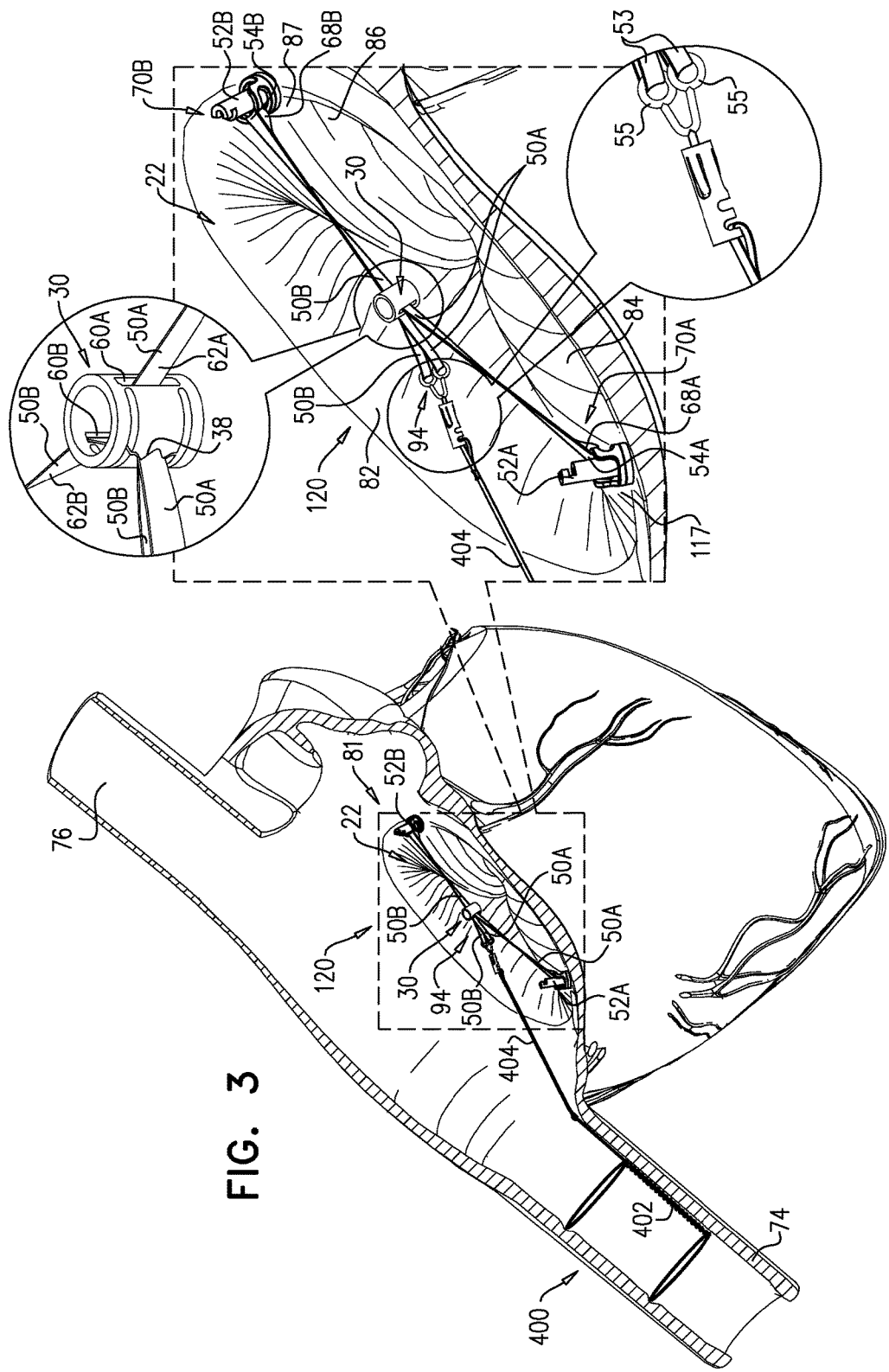
FIG. 3 is a schematic illustration of another valve-tensioning implant system, in accordance with an application of the present invention.

Reference is now made to FIG. 3, which is a schematic illustration of a valve-tensioning implant system 120, in accordance with an application of the present invention. Except as described below, implant system 120 is the same as implant system 20, described hereinabove with reference to FIGS. 1 and 2, and may incorporate any of the features thereof. In this configuration, the at least one tether 50 of implant system 120 comprises first and second tethers 50A and 50B, which (a) have first tether end portion 54A and a second tether end portion 54B, respectively, and (b) pass through (i) the portion of securing-device lumen 36 and (ii) the one-way locking opening 38. Second tissue anchor 52B is connected (e.g., permanently fixed) to second tether end portion 54B. One-way locking opening 38 is configured to (a) allow the sliding of first and second tethers 50A and 50B in the first direction through one-way locking opening 38, and (b) inhibit (e.g., prevent or limit) the sliding of first and second tethers 50A and 50B in the second direction. Tether-securing device 30 thus fixes the tethers 50 to each other.

For some applications, lateral wall 34 is shaped so as to define at least two non-constraining openings 60, such as first and second non-constraining openings 60A and 60B, disposed at respective circumferential locations different from the circumferential location of one-way locking opening 38. First and second non-constraining openings 60A and 60B are sized and shaped to allow free sliding therethrough of first and second tethers 50A and 50B, respectively. First and second tethers 50A and 50B slidably pass through first and second non-constraining openings 60A and 60B, respectively. For some applications, non-constraining openings 60 are shaped as respective slits (as shown), circles (not shown), or other shapes. For some applications in which the non-constraining openings are shaped as slits, the slits extend in a direction parallel to longitudinal axis 39 of tubular element 32.

For some applications, free end portions 53 of first and second tethers 50A and 50B (opposite first and second tether end portions 54A and 54B) are connected, typically during the implantation procedure, to fixation tether 404, described hereinbelow with reference to FIGS. 8A-C, such as by respective rings 55. Alternatively, for some applications, any excess length of the free end portions is cut and removed from the atrium, using a cutting tool, such as thoracoscopic scissors, as known in the art.

Reference is made to FIGS. 1 and 3. For applications in which the at least one tether 50 comprises single tether 50, such as exactly one tether 50 (as shown in FIG. 1), the single tether typically has a length, measured between first tissue anchor 52A and second tissue anchor 52B, of at least 30 mm, no more than 160 mm, and/or between 30 and 160 mm. For some applications, looped middle portion 88 has a length, measured along tether 50 (i.e., if the looped middle portion were to be straightened), of at least 5 mm. For application in which the at least one tether 50 comprises two tethers 50A and 50B, such as shown in FIG. 3, each of tethers 50 typically has a length of at least 20 mm, no more than 80 mm, and/or between 20 and 80 mm. Because each tether 50 typically has a high tensile strength, the length thereof does not vary based on the particular disposition of the tether at any given point in time. In other words, the length of the tether does not depend on the amount of force applied to it.

Figure 4A:
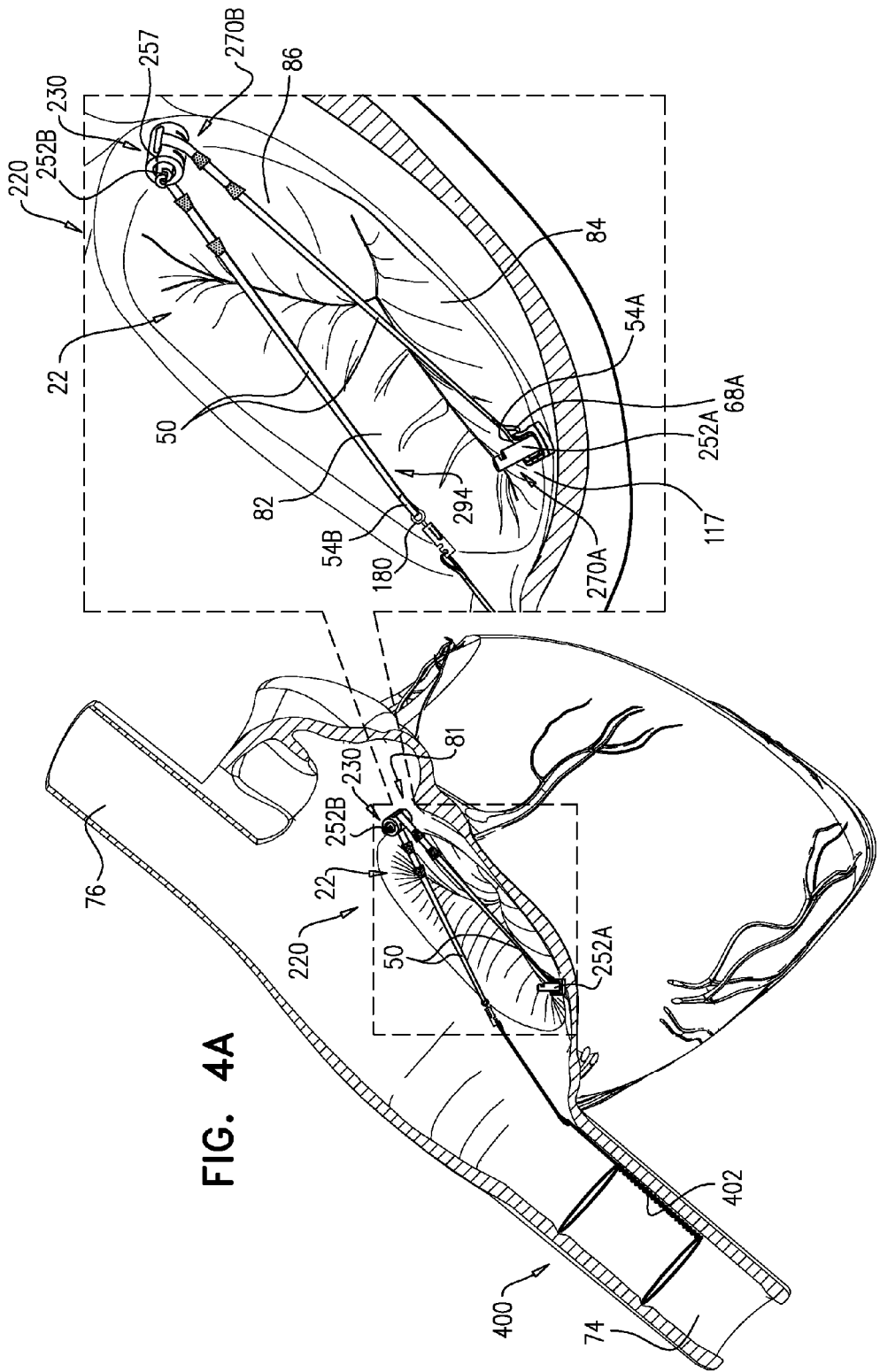
FIGS. 4A-C are schematic illustrations of yet another valve-tensioning implant system, in accordance with an application of the present invention.
Figure 4B:
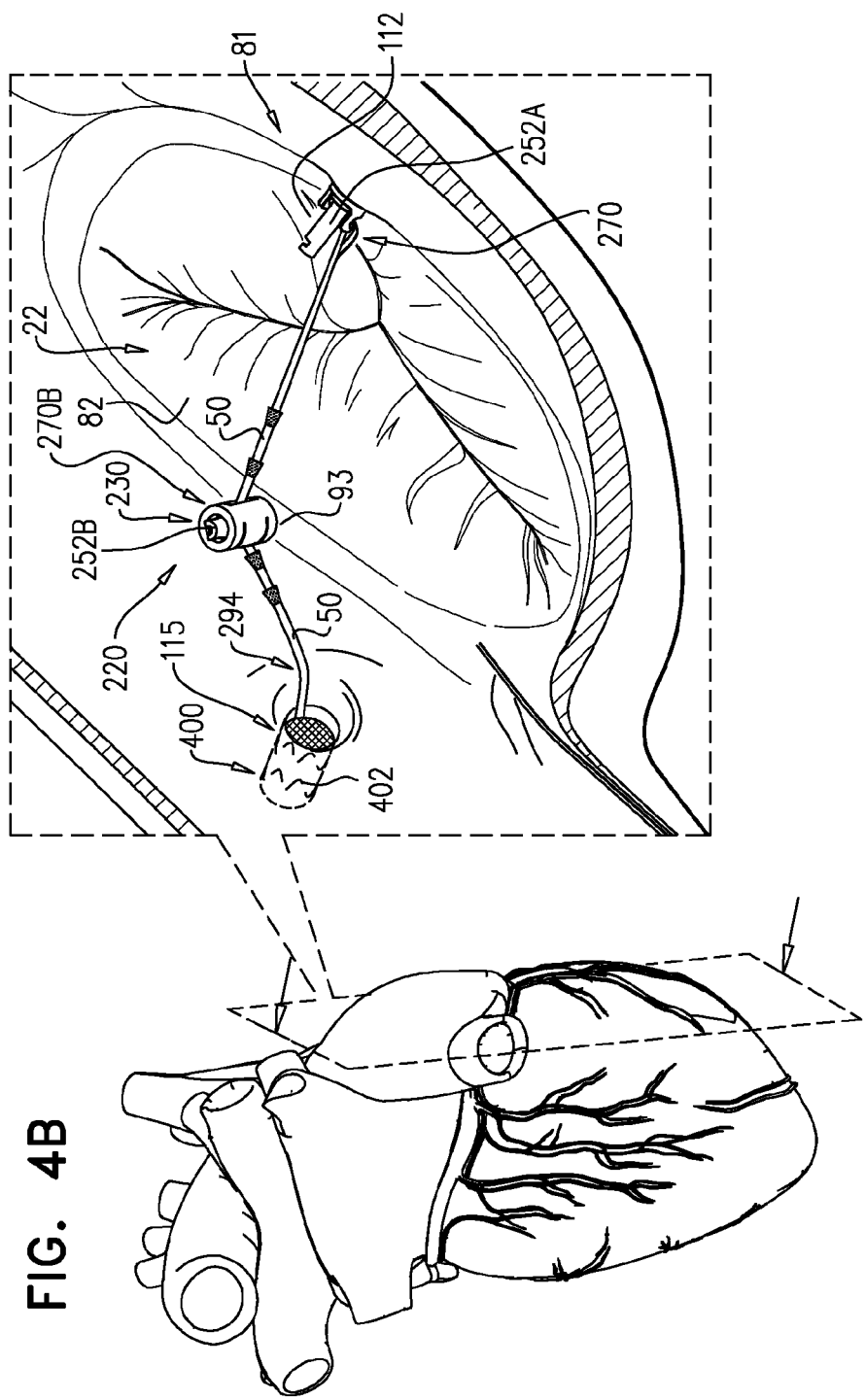
Figure 4C:
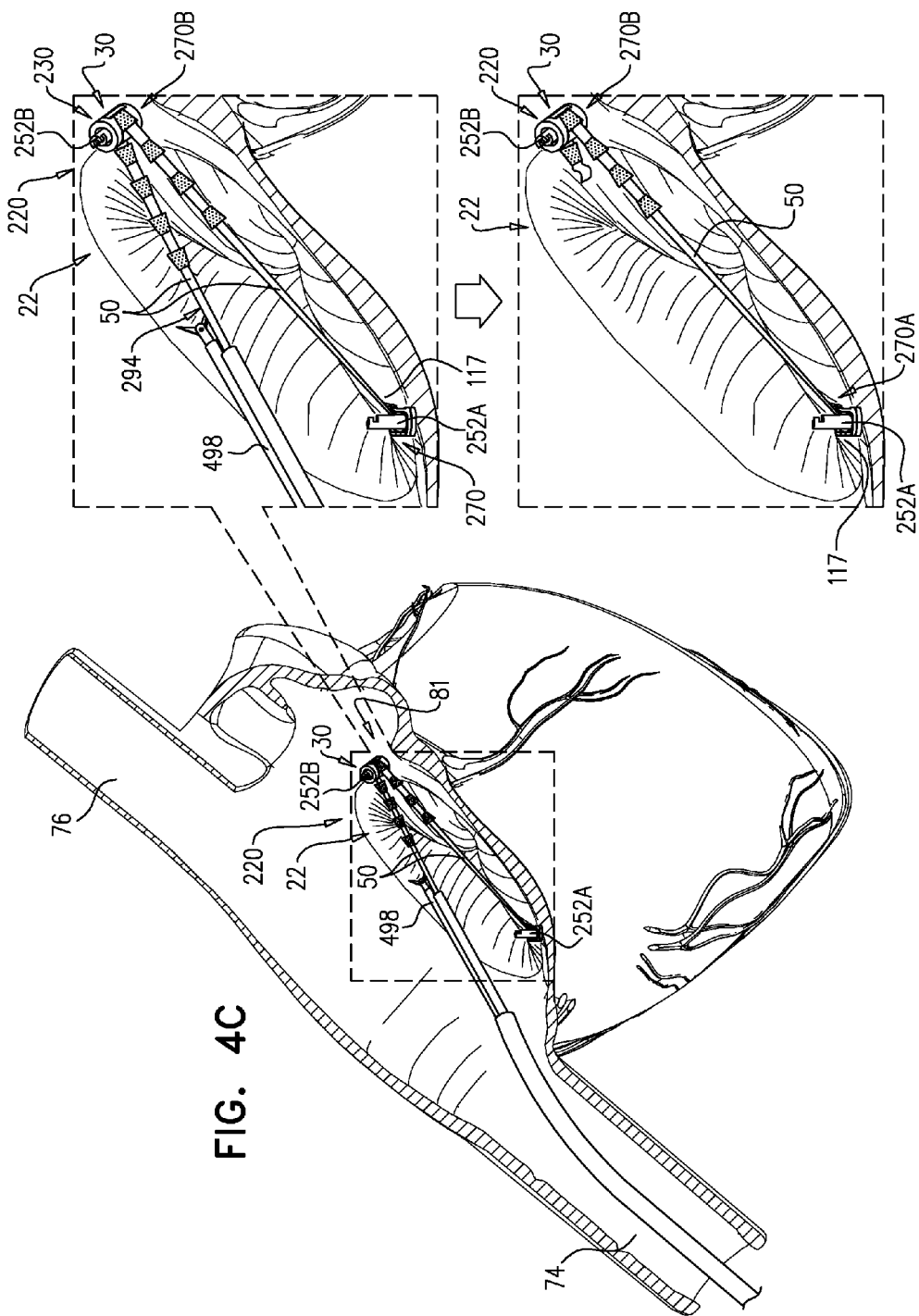

Reference is now made to FIGS. 4A-C, which are schematic illustrations of a valve-tensioning implant system 220, in accordance with an application of the present invention. Valve-tensioning implant system 220 is configured to repair an atrioventricular valve of a subject (e.g., tricuspid valve 22 or a mitral valve), using tension applied between multiple (e.g., two) anchors of the implant. Typically, repair of the atrioventricular valve facilitates a reduction in atrioventricular valve regurgitation by altering the geometry of the atrioventricular valve and/or by altering the geometry of the wall of the right or left atrium of a heart of the subject. Implant system 220 comprises a tether-securing device 230, at least one tether 50, and first and second tissue anchors 252A and 252B. Except as described below, tether-securing device 230 is similar to tether-securing device 30, described hereinabove with reference to FIGS. 1 and 2, and may incorporate any of the features thereof.

Reference is still made to FIGS. 4A-C, and is additionally made to FIG. 5, which is a schematic illustration of tether-securing device 230 fixed to second tissue anchor 252B, in accordance with an application of the present invention. Second tissue anchor 252B comprises a head 253 and a tissue-coupling element 255, such as a helical tissue-coupling element. Tether-securing device 230 is fixed to head 253, typically such that the tether-securing device surrounds at least a portion of the head. Typically, tether-securing device 230 is configured to rotate with respect to head 253, such that the tether-securing device is mounted rotatably on the head.

Typically, first tissue anchor 252A is connected (e.g., permanently fixed) to first tether end portion 54A of tether 50. For some applications, first tether end portion 54A is configured so as to define anchor-fixing loop 68A, which passes through a corresponding interface on first tissue anchor 52A so as to connect (e.g., permanently fix) the tether end portion to the tissue anchor.

In this configuration, typically a single tether 50 of the at least one tether 50 has first and second tether end portions 54A and 54B. (The at least one tether 50 may or may not comprise additional tethers in addition to the single tether.) A longitudinal portion 257 of single tether 50 passes through (a) securing-device lumen 36 and (b) one-way locking opening 38 of tether-securing device 230. For some applications, the at least one tether 50 comprises exactly one tether 50.

For some applications, lateral wall 34 of tether-securing device 230 is shaped so as to define a non-constraining opening 60, such as exactly one non-constraining opening 60, as shown in FIG. 5 (which shows two different views of the same tether-securing device and anchor). Non-constraining opening 60 is disposed at a circumferential location different from the circumferential location of one-way locking opening 38, such as diametrically opposite the locking opening. Non-constraining opening 60 is sized and shaped to allow free sliding therethrough of longitudinal portion 257. Longitudinal portion 257 of tether 50 slidably passes through non-constraining opening 60. For some applications, non-constraining opening 60 is shaped as a slit (as shown), a circle (not shown), or another shape. For some applications in which the non-constraining opening is shaped as a slit, the slit extends in a direction parallel to longitudinal axis 39 of tubular element 32 of tether-securing device 230.

Valve-tensioning implant system 120 is typically implanted transcatheterly, using a delivery system comprising one or more catheters introduced with the aid of a guidewire, through vasculature of the subject, such as (a) via the femoral vein, through inferior vena cava 74, and into right atrium 81, (b) via the basilic vein, through the subclavian vein through superior vena cava 76, and into right atrium 81, or (c) via the external jugular vein, through the subclavian vein through superior vena cava 76, and into right atrium 81. The procedure is typically performed with the aid of imaging, such as fluoroscopy, transesophageal, transthoratic echocardiography, IVUS, and/or echocardiography. The procedure may be performed using techniques described in US Patent Application Publication 2012/0035712, which is assigned to the assignee of the present application and is incorporated herein by reference, with reference to FIGS. 1A-D thereof, mutatis mutandis, and/or using techniques described hereinbelow with reference to FIGS. 11-12C.

First and second tissue anchor 252A and 252B are implanted at respective different second atrial sites 270A and 270B, each of which sites is selected from the group of sites consisting of: an annulus of tricuspid valve 22, and a wall of the right atrium of the heart above the annulus. For applications in which first and second tissue anchors 252A and 252B comprise respective helical tissue-coupling elements, the helical tissue-coupling elements are rotated into tissue at the sites, respectively. For example, as shown in FIGS. 4A and 4C, first tissue anchor 252A may be implanted within 1 cm of the point on the annulus that circumferentially corresponds to septoposterior commissure 117, and second tissue anchor 352B may be implanted at any pair of locations around the annulus of the tricuspid valve, e.g. diametrically opposed, for instance, as shown in FIG. 4B, first tissue anchor 252A may be implanted within 1 cm of the point on the annulus that circumferentially corresponds to anteroposterior commissure 112, and second tissue anchor 252B may be implanted within 1 cm of the point on the annulus that circumferentially corresponds to a circumferential middle 93 of septal leaflet 82. The direction of the 1 cm from the described anatomical sites may be either circumferentially around the annulus, up the wall of right atrium 81 above annulus 83, or a combination of circumferentially around the annulus and up the wall of the atrium.

The size of the tricuspid valve orifice is reduced by tensioning tether 50, so as to reduce regurgitation. Such tensioning may be performed by proximally pulling on second tether end portion 54B of tether 50, such that a portion of tether 50 is pulled through one-way locking opening 38. For example, a flexible longitudinal guide member 390 (as shown below in FIG. 6C) may be removably coupled to second tether end portion 54B by a loop 180, such as a ring, using techniques described in US Patent Application Publication 2013/0018459, which is assigned to the assignee of the present application and is incorporated herein by reference, with reference to FIGS. 23-26 thereof, mutatis mutandis (in which flexible longitudinal guide member 2616 corresponds to flexible longitudinal guide member 390 of the present application). Once the tension has been applied, one-way locking opening 38 maintains the tension.

After tether 50 has been tensioned, an excess portion 294 of tether 50, including second tether end portion 54B, remains free in right atrium 81. It is generally undesirable to leave this excess portion free to move around in the atrium. For some applications, excess portion is secured in a desired disposition in the vasculature of right atrium 81, such as in inferior vena cava 74 (as shown in FIG. 4A), superior vena cava 76 (such as shown in FIG. 8B, mutatis mutandis), or a coronary sinus 115 (such as shown in FIG. 4B). Techniques described hereinbelow with reference to FIGS. 8A-C may be used for such securing, mutatis mutandis. It is noted that in this configuration, venous tissue anchor 400, described hereinbelow with reference to FIGS. 8A-C, is deployed such that only a moderate amount of tension is applied to fixation tether 404, which tension is insufficient to alter the geometry of the atrium. Fixation tether 404 is connected, typically during the implantation procedure, to tether end portion 54B, such as by loop 180, e.g., a ring. Alternatively, excess portion 294 of tether 50 is cut and removed from the atrium, using a cutting tool 498, such as thoracoscopic scissors, as known in the art.

Figure 6A:
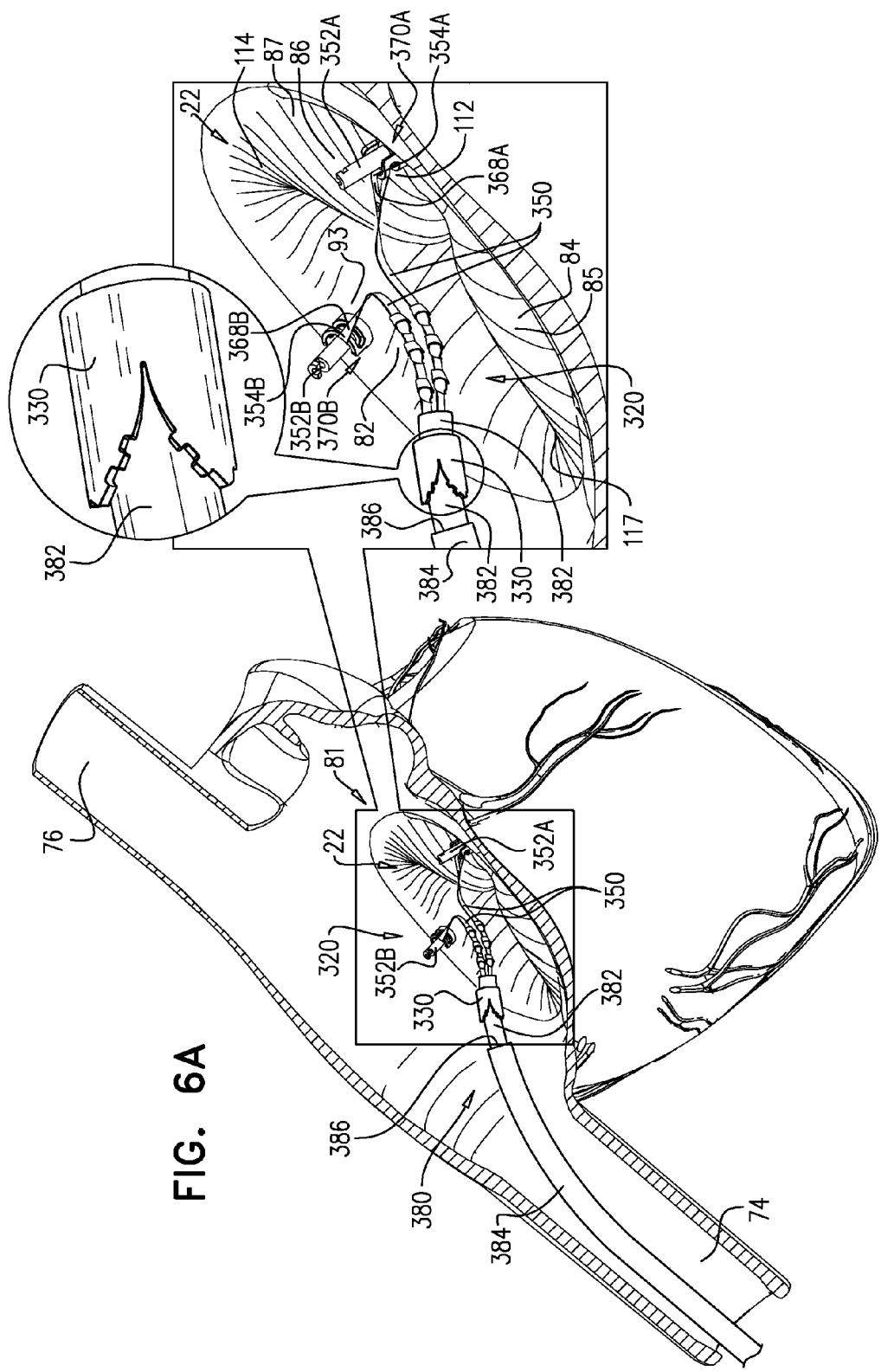
FIGS. 6A-C are schematic illustration of still another valve-tensioning implant system, in accordance with an application of the present invention.
Figure 6B:
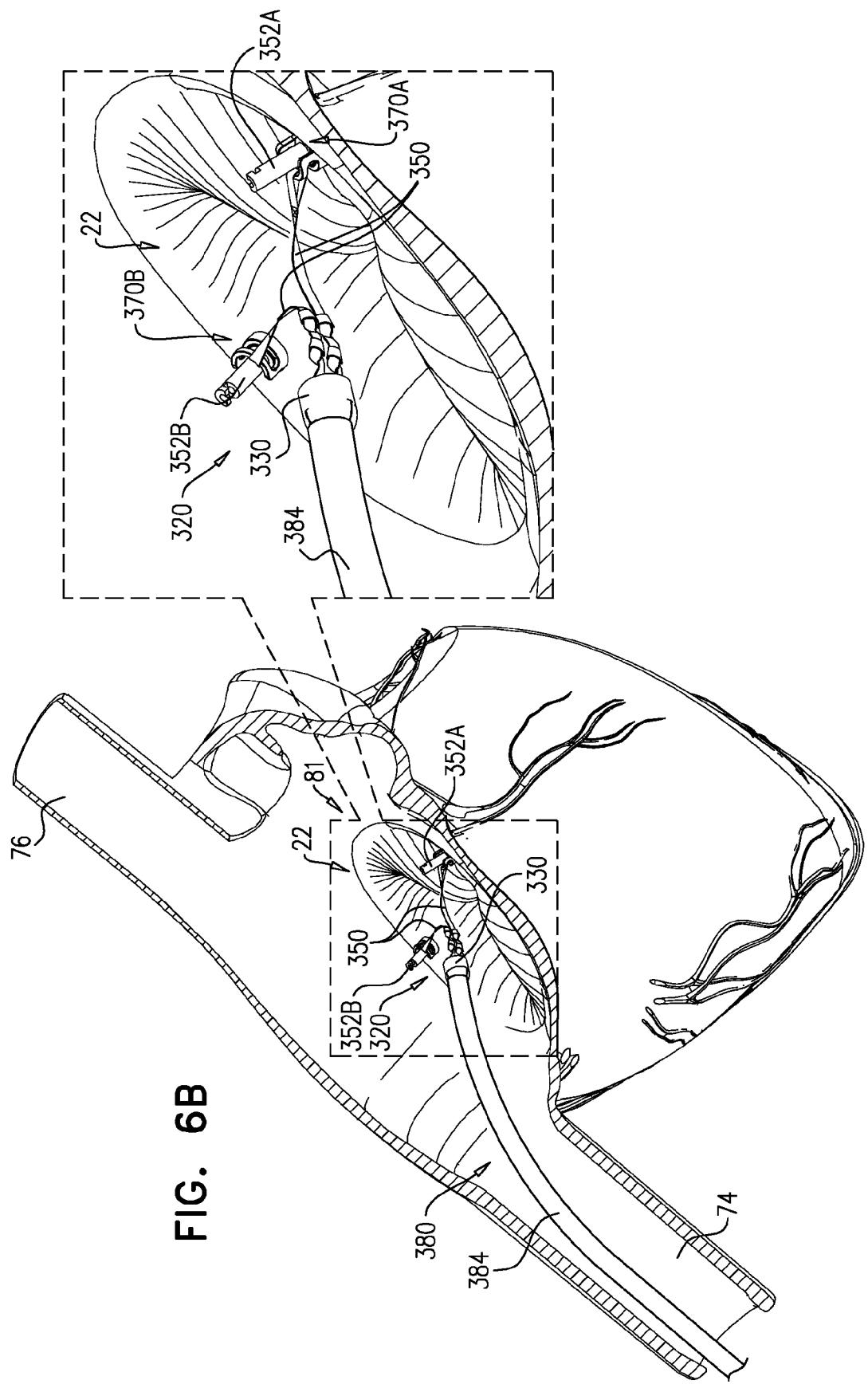
Figure 6C:
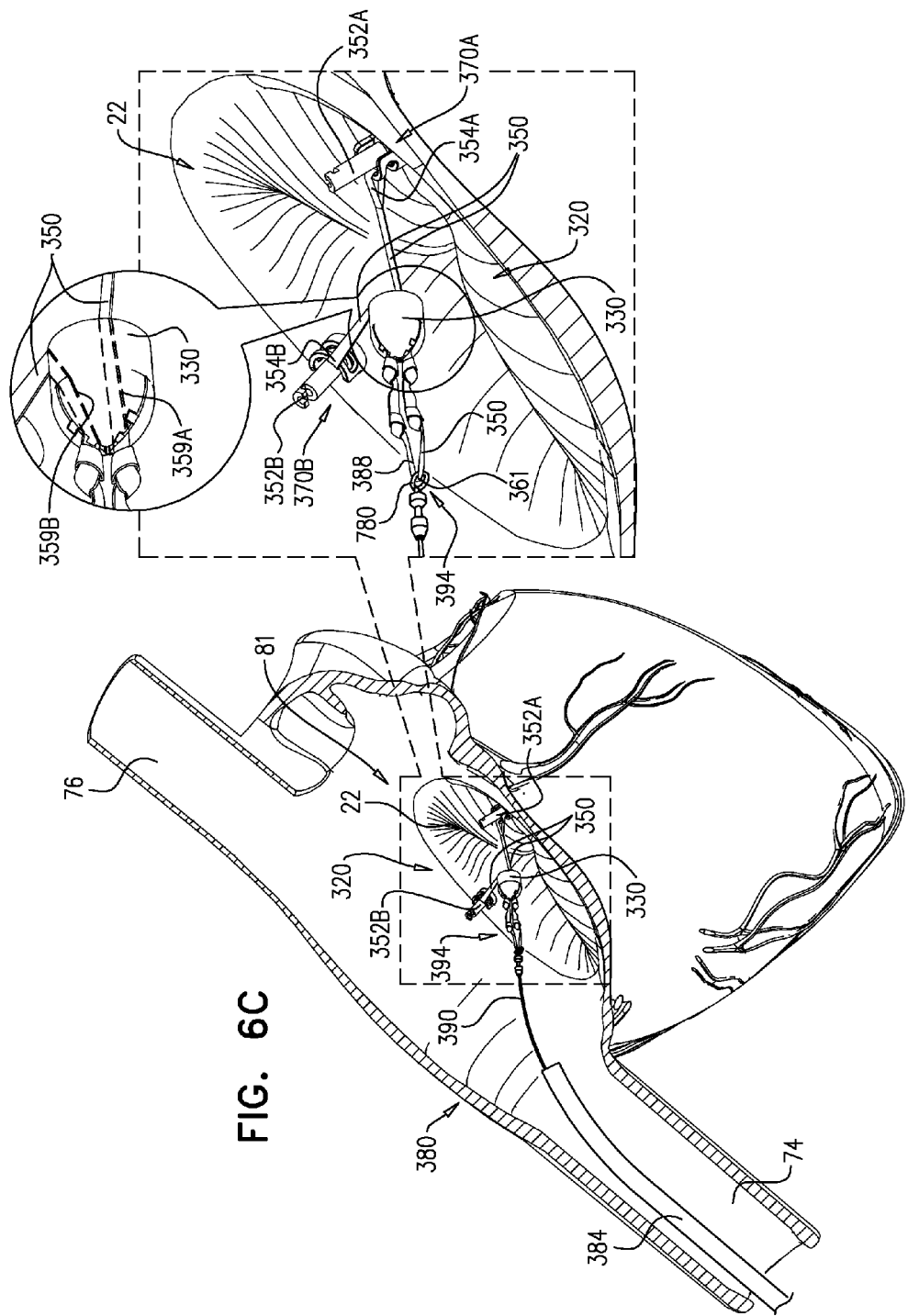

Reference is now made to FIGS. 6A-C, which are schematic illustration of a valve-tensioning implant system 320, in accordance with an application of the present invention. Valve-tensioning implant system 320 is configured to repair an atrioventricular valve of a subject (e.g., tricuspid valve 22 or a mitral valve), using tension applied between multiple (e.g., two) anchors of the implant. Typically, repair of the atrioventricular valve facilitates a reduction in atrioventricular valve regurgitation by altering the geometry of the atrioventricular valve and/or by altering the geometry of the wall of the right or left atrium of a heart of the subject. Implant system 320 comprises a tether-securing device 330, at least one tether 350, and first and second tissue anchors 352A and 352B. For some applications, first and second tissue anchors 352A and 352B are connected (e.g., permanently fixed) to first and second tether end portions 354A and 354B of the at least one tether 350, respectively (typically first and second tissue anchors 352A and 352B are connected to first and second ends of the at least one tether 350, respectively). For some applications, first and second tether end portions 354A and 354B are configured so as to define anchor-fixing loops 368A and 368B, respectively, which pass through corresponding interfaces on first and second tissue anchors 352A and 352B, respectively, so as to connect (e.g., permanently fix) the tether end portions to the tissue anchors.

Figure 7A:
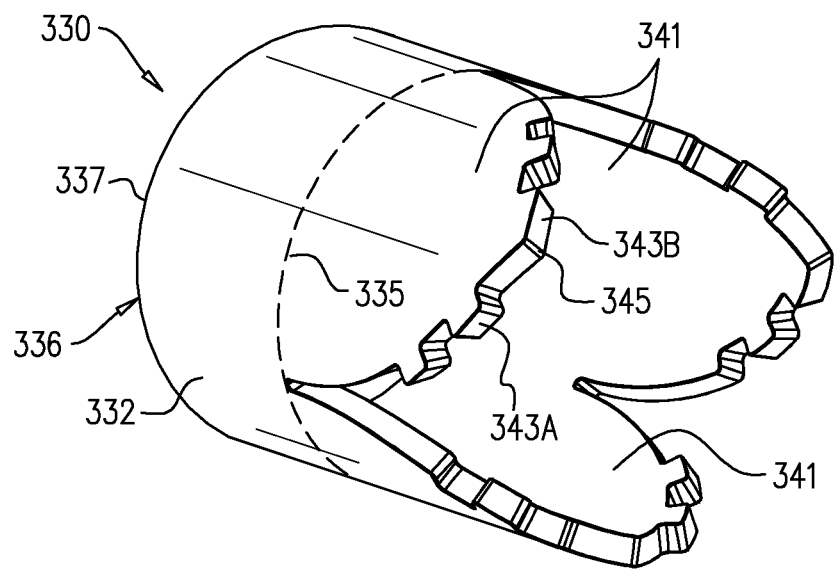
FIGS. 7A and 7B are schematic illustration of a tether-securing device of the implant system of FIGS. 6A-C, in unlocked and one-way-locked configurations, respectively, in accordance with an application of the present invention.
Figure 7B:
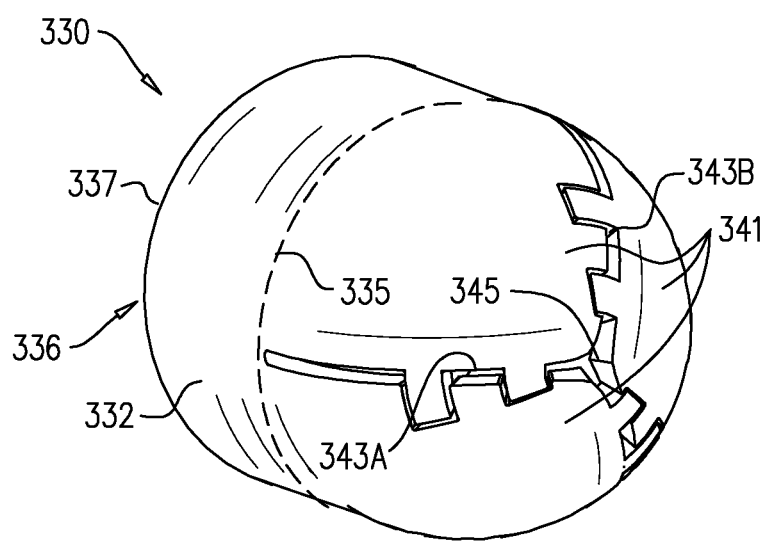

Reference is now made to FIGS. 7A and 7B, which are schematic illustration of tether-securing device 330, in unlocked and one-way-locked configurations, respectively, in accordance with an application of the present invention. Tether-securing device 330 is configured to assume the unlocked and the one-way-locked configurations. Tether-securing device 330 comprises a tubular element 332, which is shaped so as define a securing-device lumen 336 through which the at least one tether 350 passes, and has proximal and distal tube ends 335 and 337. Tether-securing device 330 typically comprises an implantable alloy, typically superelastic, such as Nitinol.

Tether-securing device 330 further comprises three or more locking pieces 341 (which may be considered pawls), which extend proximally from proximal end 335 of tubular element 332. Tether-securing device 330 is configured:
  to assume the unlocked configuration when locking pieces 341 are in a constrained state, as shown in FIG. 7A, in which locking pieces 341 extend proximally and allow distal and proximal sliding of the at least one tether 350 through securing-device lumen 336, and
  to assume the one-way-locked configuration when locking pieces 341 are in a relaxed state, as shown in FIG. 7B, in which locking pieces 341 extend proximally and radially inward toward one another (and, typically, toward a central longitudinal axis of tubular element 332). When tether-securing device 330 is in the one-way-locked configuration, locking pieces 341 (a) inhibit (e.g., prevent) the distal sliding more than when in the constrained state and, optionally, (b) allow the proximal sliding. In this relaxed state, tether-securing device 330 may be bullet-shaped, such as shown in FIG. 7B, with the locking pieces collectively defining a round nose thereof.

For some applications, such as shown in FIG. 6A-C, a single tether 350 of the at least one tether 350 has first and second tether end portions 354A and 354B. (The at least one tether 350 may or may not comprise additional tethers in addition to the single tether.) For these applications, single tether 350 typically comprises at least the following non-overlapping longitudinal portions disposed in sequence along the single tether:
  first tether end portion 354A,
  a first portion 359A that passes through securing-device lumen 336,
  a looped middle portion 388 that extends out of and away from the lumen, and then loops back to the lumen (such that a longitudinal center 361 of looped middle portion 388 is not in direct physical contact with any portion of tether-securing device 330),
  a second portion 359B that passes through securing-device lumen 336, and
  second tether end portion 354B.

Typically, the single tether comprises additional longitudinal portions between the above-listed portions, i.e., the above-listed portions are in sequence, but not contiguous with one another. For example, the single tether typically comprises a longitudinal portion between first tether end portion 354A and first portion 359A, and a longitudinal portion between second portion 359B and second tether end portion 354B.

Tether-securing device 330 thus fixes first and second portions 359A and 359B to each other, either (a) directly, if the two portions touch one another between locking pieces 341, or (b) indirectly, via the tether-securing device, if the two portions do not touch one another in the one-way locking opening (such as if they are at different circumferential positions around the tether-securing device). For some applications, the at least one tether 350 comprises exactly one tether 350. For applications in which the at least one tether 350 comprises two tethers 350, such as described hereinbelow with reference to FIG. 9, tether-securing device 330 thus fixes the tethers 350 to each other, either (a) directly, if the two tethers touch one another between locking pieces 341, or (b) indirectly, via the tether-securing device, if the two tethers do not touch one another in the one-way locking opening (such as if they are at different circumferential positions around the tether-securing device).

For some applications, locking pieces 341 comprise exactly three locking pieces (as shown) or exactly four locking pieces (configuration not shown). Typically, locking pieces 341 are integral with tubular element 332, and the locking pieces and tubular element are manufactured from a single piece of material. For some applications, tubular element 332 has an inner diameter of at least 3 mm, no more than 12 mm, and/or between 3 and 12 mm, and/or an outer diameter of at least 3.1 mm, no more than 12.1 mm, and/or between 3.1 and 12.1 mm.

For some applications, each of locking pieces 341 is shaped so as to define two curved proximal edges 343A and 343B that meet at a proximal tip 345. For some applications, proximal edges 343A and 343B are shaped so as to define uneven edge surfaces, which, for example, may be jagged or serrated. The uneven edge surfaces of proximal edge 343A interconnect with the uneven edge surfaces of proximal edge 343B, thereby creating friction on the at least one tether 350 and inhibiting (e.g., preventing) sliding of the at least one tether through the tether-securing device, at least in the distal direction. For some applications, the uneven edge surfaces are shaped as define teeth, such as shown in FIG. 7A-B. Alternatively or additionally, for some applications, the uneven edge surfaces are rough. For some applications, locking pieces 341 are convex, as viewed from outside tether-securing device 330, at least when locking pieces 341 are in the relaxed state.

In the relaxed state, such as shown in FIG. 7B, proximal tips 345 of locking pieces may be in a vicinity of each other, e.g., within 2 mm of each other, if not held farther apart from each other by tether 350 (which is not shown in FIG. 7B). For example the tips may be within 0.1 mm of each other, or touching each other.

For some applications, as shown, tubular element 332 is cylindrical. Alternatively, the tubular element has another shape. For some applications, an axial length of tubular element 332 is at least 3 mm, no more than 50 mm, and/or between 3 and 50 mm; an axial length of tether-securing device 330 when in the unlocked configuration is between 3 and 50 mm; and/or an axial length of tether-securing device 330 when in the one-way-locked configuration is between 3 and 50 mm.

Reference is again made to FIGS. 6A-C. For some applications, a delivery tool 380 is provided, which comprises an inner catheter shaft 382, which is configured to apply a constraining force to tether-securing device 360 when inner shaft 382 is disposed in the securing-device lumen 336, as shown in FIG. 6A. The constraining force retains tether-securing device 360 in the unlocked configuration. Inner shaft 382 is shaped so as to define a shaft lumen, through which the at least one tether 350 removably slidably passes. Typically, an outer diameter of inner shaft 382 is between 80% and 99% of an inner diameter of tubular element 332 of tether-securing device 330. Typically, delivery tool 380 further comprises an outer shaft 384, which surrounds inner shaft 382. Typically, an inner diameter of outer shaft 384 is between 80% and 99% of an outer diameter of tubular element 332 of tether-securing device 330.

Valve-tensioning implant system 320 is typically implanted transvascularly, using a delivery system comprising one or more catheters introduced with the aid of a guidewire, through vasculature of the subject, such as (a) via the femoral vein, through inferior vena cava 74, and into right atrium 81, (b) via the basilic vein, through the subclavian vein through superior vena cava 76, and into right atrium 81, or (c) via the external jugular vein, through the subclavian vein through superior vena cava 76, and into right atrium 81. The procedure is typically performed with the aid of imaging, such as fluoroscopy, transesophageal, transthoracic echocardiography, IVUS, and/or echocardiography. The procedure may be performed using techniques described in US Patent Application Publication 2012/0035712, which is assigned to the assignee of the present application and is incorporated herein by reference, with reference to FIGS. 1A-D thereof, mutatis mutandis, and/or using techniques described hereinbelow with reference to FIGS. 11-12C.

At the beginning of the procedure, tether-securing device 330 resides on inner shaft 382, such that the inner shaft holds locking pieces 341 in the constrained state, and tether-securing device 330 in the unlocked configuration. A distal end 386 of outer shaft 384 is held by the surgeon proximal to a proximal end of tether-securing device 330. Typically, tether-securing device 330 is delivered to a vicinity of the target site (e.g., to right atrium 81) with the at least one tether 350 pre-threaded through securing-device lumen 336.

As shown in FIG. 6A, first and second tissue anchors 352A and 352B are implanted at respective different implantation sites 370A and 370B, each of which sites is selected from the group of sites consisting of: an annulus of tricuspid valve 22, and a wall of the right atrium of the heart above the annulus. For applications in which first and second tissue anchors 52A and 52B comprise respective helical tissue-coupling elements, the helical tissue-coupling elements are rotated into tissue at the sites, respectively. Implantation techniques described hereinbelow with reference to FIGS. 11-12C may optionally be used. For example, first and second tissue anchors 352A and 352B may be implanted at diametrically opposed sites on the annulus of the tricuspid valve, e.g., as shown in FIGS. 6A-C, first tissue anchor 352A may be implanted within 1 cm of the site on the annulus that circumferentially corresponds to an anteroposterior commissure 112, and second tissue anchor 352B may be implanted within 1 cm of the site on the annulus that circumferentially corresponds to a circumferential middle 93 of septal leaflet 82. Alternatively, for some applications, first and second tissue anchors 352A and 352B are implanted (a) within 1 cm of the site on the annulus that circumferentially corresponds to a septoanterior commissure 114, and within 1 cm of the site on the annulus that circumferentially corresponds to a circumferential middle of posterior leaflet 84, respectively, or (b) within 1 cm of the site on the annulus that circumferentially corresponds to a circumferential middle of the annulus 87 along anterior leaflet 86, and within 1 cm of the site on the annulus that circumferentially corresponds to septoposterior commissure 117, respectively. The direction of the 1 cm from the described anatomical sites may be either circumferentially around the annulus, up the wall of right atrium 81 above annulus 83, or a combination of circumferentially around the annulus and up the wall of the atrium.

A size of a tricuspid valve orifice is reduced by tensioning tether 350, so as to reduce regurgitation. Such tensioning may be performed by distally advancing inner shaft 382 while proximally pulling on looped middle portion 388 of tether 350 (shown and labeled in FIG. 6C), such that portions of tether 350 pass through inner shaft 382 and unlocked tether-securing device 330 mounted thereon. For example, a flexible longitudinal guide member 390 may be removably coupled to looped middle portion 388 by a loop 780, such as a ring, using techniques described in US Patent Application Publication 2013/0018459, which is assigned to the assignee of the present application and is incorporated herein by reference, with reference to FIGS. 23-26 thereof, mutatis mutandis (in which flexible longitudinal guide member 2616 corresponds to flexible longitudinal guide member 390 of the present application).

After tether 350 has been tensioned, tether-securing device 330 is transitioned to the one-way-locked configuration, by holding tether-securing device 330 in place by holding inner shaft 382 in place, and distally advancing outer shaft 384, as shown in FIG. 6B. Tether-securing device 330 is pushed distally by outer shaft 384 over inner shaft 382 until locking pieces 341 are no longer constrained by inner shaft 382, such that tether-securing device 330 automatically transitions to the one-way-locked configuration (in which locking pieces 341 are in a relaxed, resting state). Since tether-securing device 330 allows proximal sliding of tether 350 therethrough even when in the one-way-locked configuration, if necessary further tension can be applied to tether 350 by pushing tether-securing device 330 distally using outer shaft 384. Once the tension has been applied, tether-securing device 330 maintains the tension.

FIG. 6C shows valve-tensioning implant system 320 after tension has been applied and tether-securing device 330 has been fully deployed. The final disposition of an excess portion 394 of tether 350 near looped middle portion 388 is described hereinbelow with reference to FIGS. 8A-C.

Reference is now made to FIGS. 8A-C, which are schematic illustrations of techniques for securing excess portion 394 of tether 350, in accordance with respective applications of the present invention. As shown in FIG. 6C, after tether 350 has been tensioned, excess portion 394 of tether 350 near looped middle portion 388 remains free in right atrium 81. It is generally undesirable to leave this excess portion free to move around in the atrium.

In some applications of the present invention, valve-tensioning implant system 320 further comprises a venous tissue anchor 400, for holding excess portion 394 secured in a desired disposition in the vasculature of right atrium 81. Venous tissue anchor 400 is configured to be implanted at an implantation site upstream of the tricuspid valve. FIGS. 8A, 8B, and 8C show venous tissue anchor 400 disposed in inferior vena cava 74, superior vena cava 76, and coronary sinus 115, respectively. Venous tissue anchor 400 is connected to excess portion 394 by a fixation tether 404, which may be connected to excess portion 394 by a loop 780, such as a ring. Such connection is typically made after the tissue anchors have been implanted and tension has been applied to tether 350, as described hereinabove with reference to FIGS. 6A-C. For some applications, such connection is made using techniques described in above-mentioned US Patent Application Publication 2013/0018459, with reference to FIGS. 23-26 thereof, mutatis mutandis. It is noted that in this configuration, venous tissue anchor 400 is deployed such that only a moderate amount of tension is applied to fixation tether 404, which tension is insufficient to alter the geometry of the atrium.

By way of example and not limitation, in the deployment configuration shown in FIG. 8A, first tissue anchor 352A is implanted within 1 cm of the site on the annulus that circumferentially corresponds to septoanterior commissure 114, and second tissue anchor 352B is implanted within 1 cm of the site on the annulus that circumferentially corresponds to septoposterior commissure 117. By way of example and not limitation, in the deployment configuration shown in FIG. 8B, first tissue anchor 352A is implanted within 1 cm of the site on the annulus that circumferentially corresponds to anteroposterior commissure 112, and second tissue anchor 352B is implanted within 1 cm of the site on the annulus that circumferentially corresponds to circumferential middle 93 of septal leaflet 82. By way of example and not limitation, in the deployment configuration shown in FIG. 8C, first tissue anchor 352A is implanted within 1 cm of the site on the annulus that circumferentially corresponds to anteroposterior commissure 112, and second tissue anchor 352B is implanted within 1 cm of the site on the annulus that circumferentially corresponds to septoanterior commissure 114. The direction of the 1 cm from the described anatomical sites may be either circumferentially around the annulus, up the wall of right atrium 81 above annulus 83, or a combination of circumferentially around the annulus and up the wall of the atrium.

For some applications, venous tissue anchor 400 comprises an intraluminal stent 402. The stent is configured to be implanted in the vein by applying an outward radial force to the wall of the vein. Typically, the stent is configured to self-expand. For example, the stent may comprise a shape-memory alloy, such as Nitinol. Alternatively, the stent comprises a deformable metal, and is expanded by a tool, such as a balloon. For some applications, stent 402 comprises a plurality of interconnected superelastic metallic struts, arranged so as to allow crimping the stent into a relatively small diameter (typically less than 8 mm) catheter, while allowing deployment to a much larger diameter (typically more than 20 mm) in the vein, while still maintaining radial force against the tissue of the wall of the vein, in order to anchor stent 402 to the wall of the vein by friction. Typically, the stent is configured to not penetrate tissue of the wall of the vein. For some applications, stent 402 implements techniques described in U.S. Provisional Application 61/783,224, filed Mar. 14, 2013, which is assigned to the assignee of the present application and is incorporated herein by reference.

For applications in which venous tissue anchor 400 is implanted in superior vena cava 76 or inferior vena cava 78, intraluminal stent 402 typically has a greatest outer diameter of at least 20 mm, no more than 50 mm, and/or between 20 and 50 mm, when unconstrained and fully radially expanded, i.e., no forces are applied to the stent by a delivery tool, walls of a blood vessel, or otherwise. For applications in which first venous tissue anchor 400 is implanted in coronary sinus 115, intraluminal stent 402 typically has a greatest outer diameter of at least 8 mm, no more than 15 mm, and/or between 8 and 15 mm, when unconstrained and fully radially expanded.

Alternatively, excess portion 394 is cut and removed from the atrium, such as using techniques described hereinbelow with reference to FIG. 9, mutatis mutandis.

Reference is now made to FIG. 9, which is a schematic illustration of a valve-tensioning implant system 420, in accordance with an application of the present invention. Except as described below, implant system 420 is the same as implant system 320, described hereinabove with reference to FIGS. 6A-C and 7A-B, and may incorporate any of the features thereof. In this configuration, the at least one tether 350 of implant system 420 comprises first and second tethers 350A and 350B, which (a) have first tether end portion 354A and a second tether end portion 354B, respectively, and (b) pass through the portion of securing-device lumen 336. Second tissue anchor 352B is connected (e.g., permanently fixed) to second tether end portion 354B.

For some applications, after tension is applied to first and second tethers 350A and 350B and tether-securing device 330 has been transitioned to the one-way-locked configuration, excess portions 494 of tethers 350A and 350B are cut and removed from the atrium, using cutting tool 498. Alternatively, excess portions 494 are held in a desired disposition, such as using techniques described hereinabove with reference to FIGS. 8A-C, mutatis mutandis.

Reference is made to FIGS. 6A-C and 9. For applications in which the at least one tether 350 comprises single tether 350, such as exactly one tether 350 (as shown in FIGS. 6A-C), the single tether typically has a length, measured between first tissue anchor 352A and second tissue anchor 352B, of at least 30 mm, no more than 160 mm, and/or between 30 and 160 mm. For some applications, looped middle portion 388 has a length, measured along tether 350 (i.e., if the looped middle portion were to be straightened), of at least 5 mm. For application in which the at least one tether 350 comprises two tethers 350A and 350B, such as shown in FIG. 9, each of tethers 350 typically has a length of at least 20 mm, no more than 80 mm, and/or between 20 and 80 mm. Because each tether 350 typically has a high tensile strength, the length thereof does not vary based on the particular disposition of the tether at any given point in time. In other words, the length of the tether does not depend on the amount of force applied to it.

Reference is now made to FIGS. 10A-D, which are schematic illustrations of friction-enhancing features of a tether 550, in accordance with respective applications of the present invention. These features may be used with tethers 50 or 350, in any of the configurations described herein with reference to FIGS. 1-2, 3, 4A-5, 6A-8C, and 9. The friction-enhancing features enhance friction between the tethers and one-way locking opening 38 of tether-securing device 30, or proximal edges 343A and 343B of locking pieces 341 of tether-securing device 330, as the case may be.

Typically, tether 550 defines a plurality of securement protrusions 560 spaced at intervals (I) along tether 550, which protrusions serve as the friction-enhancing features. The protrusions may also serve to ratchet the tether unidirectionally through one-way locking opening 38 of tether-securing device 30, or proximal edges 343A and 343B of locking pieces 341 of tether-securing device 330, as the case may be. For some applications, an average interval of securement protrusions 560 along tether 550 is at least 1 mm, no more than 5 mm, and/or between 1 and 5 mm.

Figure 10A:
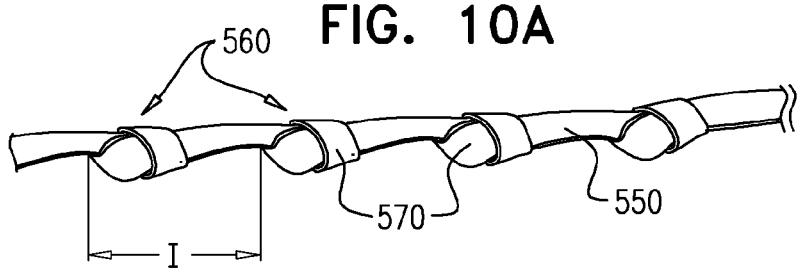
FIGS. 10A-D are schematic illustrations of friction-enhancing features of a tether, in accordance with respective applications of the present invention.
Figure 10B:
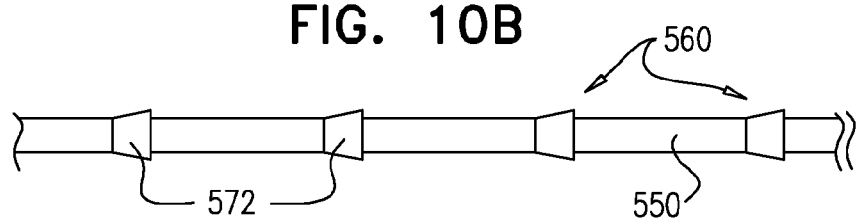
Figure 10C:
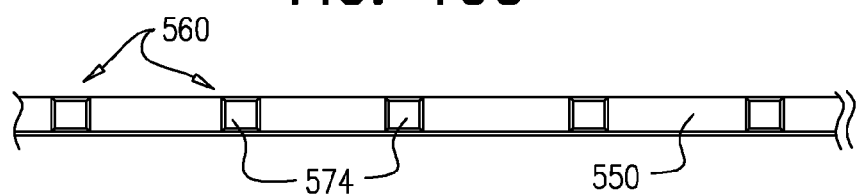
Figure 10D:
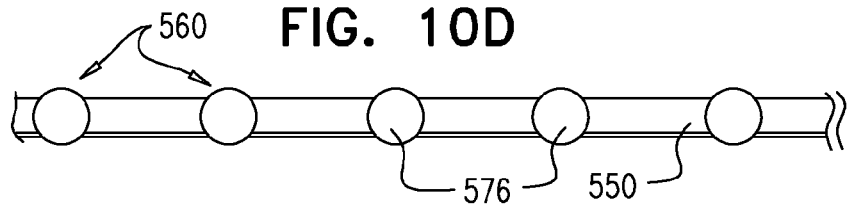

For some applications, protrusions 560 are defined by respective knots 570 in tether 550, such as shown in FIG. 10A. For some applications, protrusions 560 comprise respective cones 572 on tether 550, such as shown in FIG. 10B. For some applications, protrusions 560 comprise respective scales 574 on tether 550, such as shown in FIG. 10C. For some applications, protrusions 560 comprise respective beads 576 on tether 550, such as shown in FIG. 10D.

Figure 11:
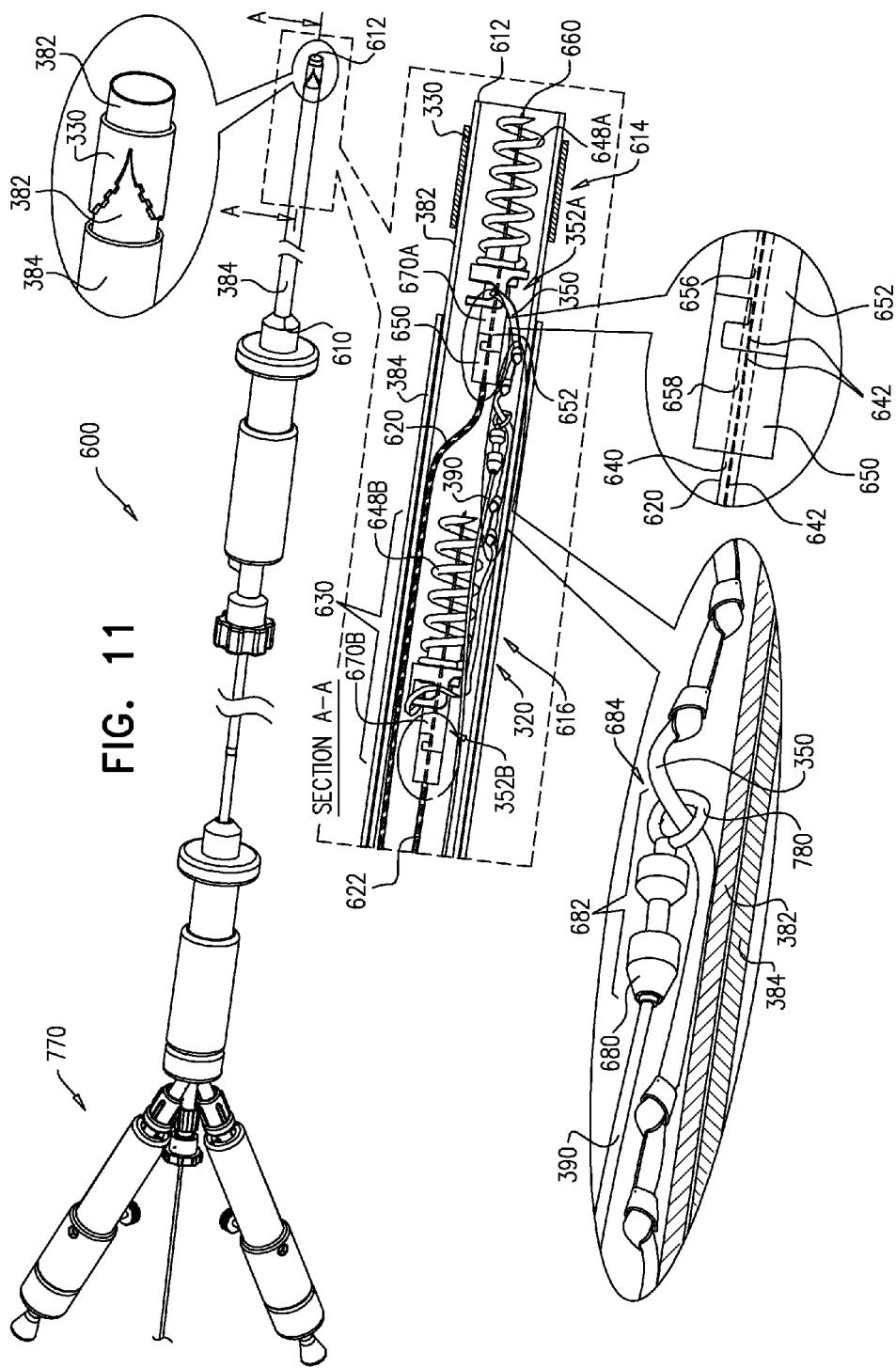
FIG. 11 is a schematic illustration of a delivery system comprising a multiple-anchor delivery tool, in accordance with an application of the present invention.

Reference is now made to FIG. 11, which is a schematic illustration of a delivery system comprising a multiple-anchor delivery tool 600, in accordance with an application of the present invention. Multiple-anchor delivery tool 600 is used to sequentially deliver and implant two or more tissue anchors of an implant system, such as implant systems 20, 120, 220, 320, and 420, described hereinabove. Although multiple-anchor delivery tool 600 is illustrated and described below with reference to implant system 320 (and thus is one implementation of delivery tool 380), described hereinabove with reference to FIGS. 6A-7B, the delivery tool may be used for delivering the other implant systems described herein, mutatis mutandis.

For some applications, implant system 320 comprises a male coupling 680 of a first flexible-longitudinal-member-coupling element 682 of an intraluminal locking mechanism 684 which is connected to a female coupling during implantation, such as in order to allow implantation of the third tissue anchor with a separate catheter delivery system, such as described in above-mentioned US Patent Application Publication 2013/0018459, for example with reference to FIGS. 25-26 thereof.

Multiple-anchor delivery tool 600 comprises outer shaft 384 and inner shaft 382. Inner shaft 382 has proximal and distal ends 610 and 612. First and second tissue anchors 352A and 352B are initially removably positioned in inner shaft 382 at first and second longitudinal locations 614 and 616, respectively. First longitudinal location 614 is more distal than second longitudinal location 616. In other words, the tissue anchors are initially positioned in the desired sequence of deployment in inner shaft 382, with the first anchor to be deployed positioned more distally than the subsequent anchor(s) to be deployed. The tissue anchors are interconnected by tether 350.

Multiple-anchor delivery tool 600 further comprises first and second torque cables 620 and 622, which (a) are removably coupled to first and second heads 670A and 670B of first and second tissue anchors 352A and 352B, respectively, (b) extend within inner shaft 382 proximally from first and second heads 670A and 670B, respectively, and (c) transmit torque when rotated, for rotating tissue-coupling elements 648A and 648B of first and second tissue anchors 352A and 352B, respectively, into tissue. Typically, the torque cables additionally transmit axial force, to enable pushing of the tissue-coupling elements 648A and 648B into the tissue as they are rotated. A portion 630 of first torque cable 620 is initially removably positioned alongside second tissue anchor 352B in inner shaft 382. Thus each anchor is separately connected to a control handle 770 by its own torque cable, which allows full and separate control of deployment of each anchor by an operator of the multiple-anchor delivery tool.

For some applications, implant system 320 comprises one or more additional tissue anchors, and tool 600 correspondingly comprises one or more additional torque cables, removably coupled to the tissue coupling elements, as described herein. These additional tissue anchors are initially removably positioned in inner shaft 382 proximal to second longitudinal location 616. For example, implant system 320 may further comprise a third tissue anchor, which comprises (a) a third helical tissue coupling elements, and (b) a third head, which comprises a third tether interface; the tether is coupled to (e.g., slidably coupled to) the third tether interface; the third tissue anchor is removably positioned in inner shaft 382 at a third longitudinal location that is more proximal than second longitudinal location 616; and multiple-anchor delivery tool 600 further comprises a third torque cable, which (a) is removably coupled to the third head, (b) extends within the inner shaft proximally from the third head, and (c) transmits torque when rotated, wherein a portion of the second torque cable is removably positioned alongside the third tissue anchor in the inner shaft.

For some applications, first torque cable 620 is shaped so as to define a lumen 640 therethrough, and multiple-anchor delivery tool 600 further comprises a sharpened wire 642, which removably passes through lumen 640. A distal end of first torque cable 620 comprises a distal coupling element 650, which is configured to be removably coupled to a corresponding proximal coupling element 652 defined by a proximal portion of first head 670A. Distal and proximal coupling elements 650 and 652 are shaped so as to define corresponding interlocking surfaces, such that the coupling elements interlock, thereby mating the coupling elements to one another. First head 670A, including proximal coupling element 652, is shaped so as to define a first longitudinal channel 656 at least partially therethrough (typically entirely therethrough), which channel is coaxial with first head 670A. Distal coupling element 650 is shaped so as to define a second longitudinal channel 658 therethrough, which is coaxial with lumen 640 of first torque cable 620. First and second channels 656 and 658 are radially aligned with one another. When a portion of sharpened wire 642 is positioned in these channels, the sharpened wire prevents decoupling of distal coupling element 650 from proximal coupling element 652. Upon removal of sharpened wire 642 from channels 656 and 658 and the coupling elements 650 and 652, the coupling elements are free to be decoupled from one another.

For some applications, sharpened wire 642 is shaped so as to define a sharp distal tip 660. For these applications, first tissue anchor 352A typically is helical, and sharpened wire 642 is initially removably positioned within a channel defined by the helix. As tissue anchor 352A is screwed into tissue, sharpened wire 642 penetrates and advances into the tissue along with the anchor to a certain depth in the tissue. For some applications, when the shaft penetrates to the certain depth, the sharpened wire is withdrawn slightly. Typically, after tissue anchor 352A has been fully implanted, sharpened wire 642 is withdrawn entirely from the tissue, and removed from the patient's body. Optionally, the sharp distal tip of sharpened wire 642 is inserted into the tissue slightly, even before insertion of tissue anchor 352A, in order to prevent sliding of the tissue-coupling element on the surface of the tissue before commencement of insertion of the tissue-coupling element into the tissue.

After implantation of tissue anchor 352A, sharpened wire 642 is withdrawn proximally from the channel of tissue anchor 352A and from channels 656 and 658 of distal and proximal coupling elements 650 and 652, thereby decoupling the coupling elements from one another, and decoupling first torque cable 620 from first head 670A. After such proximal withdrawal, sharpened wire 642 typically remains within lumen 640 of first torque cable 620.

Figures 12A, 12B, 12C:
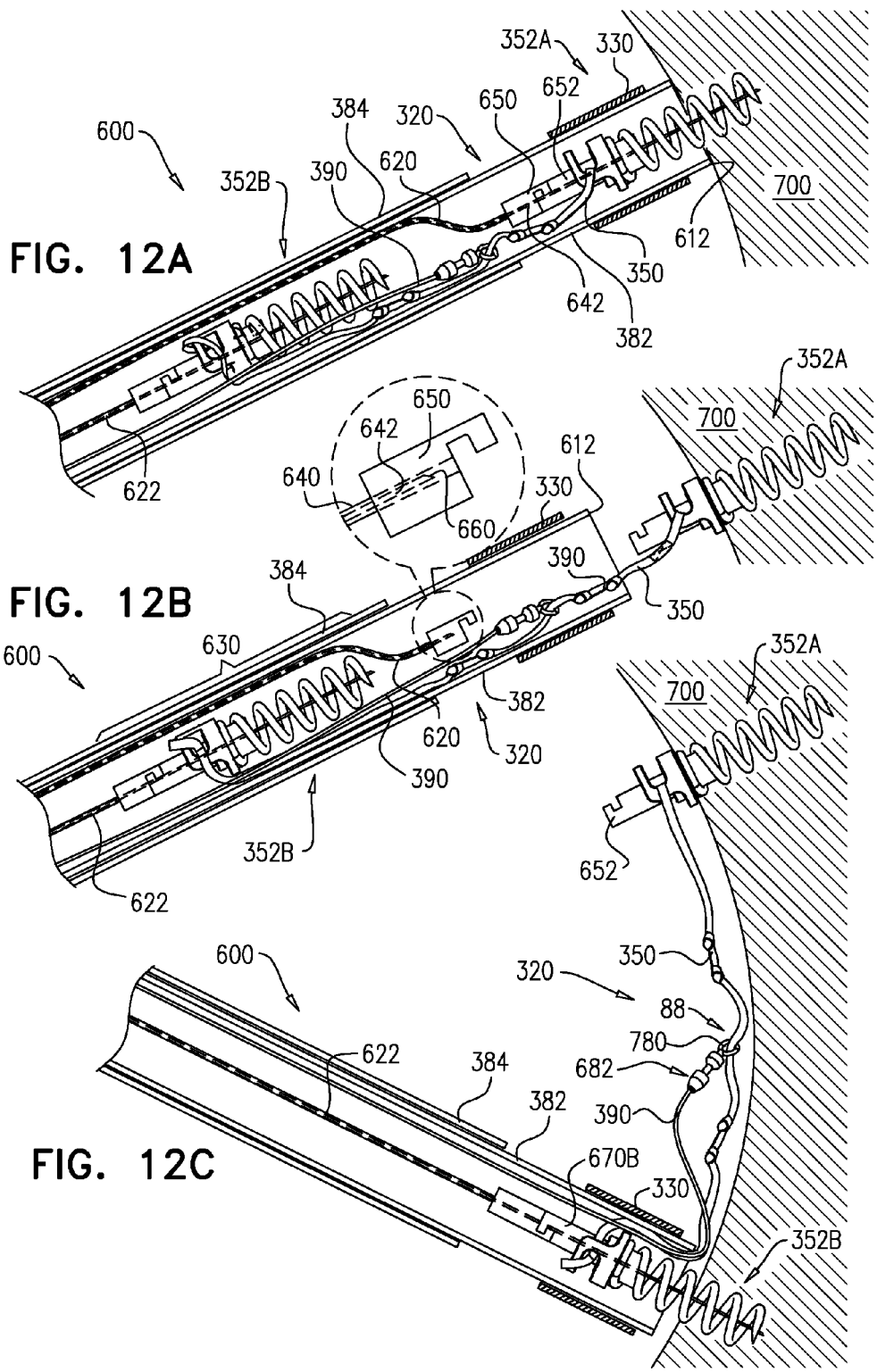
FIGS. 12A-C are schematic illustrations of a deployment method using the multiple-anchor delivery tool of FIG. 11, in accordance with an application of the present invention.

For some applications, the decoupling of first torque cable 620 and first head 670A is performed alternatively or additionally using techniques described in US Patent Application Publication 2012/0035712, which is assigned to the assignee of the present application and is incorporated herein by reference, such as with reference to FIGS. 12A-C thereof.

Second torque cable 622 and second tissue anchor 352B similarly comprise the above-mentioned elements (e.g., the sharpened wire and coupling elements), and are similarly configured, as do any additional torque cables and tissue anchors that may be provided, as described above.

Multiple-anchor delivery tool 600 further comprises control handle 770, which is configured to control the deployment of the tissue anchors, by rotating the torque cables, distally advancing the anchors through inner shaft 382, and proximally withdrawing the sharpened wires and torque cables. Control handle 770 may implement features of handle portion 1004, described with reference to FIG. 11C of above-mentioned US Patent Application Publication 2012/0035712, mutatis mutandis.

Reference is now made to FIGS. 12A-C, which are schematic illustrations of a deployment method using multiple-anchor delivery tool 600, in accordance with an application of the present invention. Although this method is described for deploying first and second tissue anchors 352A and 352B, the method may also be used to deploy first and second tissue anchors 52A and 52B, first and second tissue anchors 252A and 252B, or first and second tissue anchors 352A and 352B, described hereinabove, or other tissue anchors. Inner shaft 382 and outer shaft 384 are typically advanced transvascularly, using a delivery system comprising one or more catheters introduced with the aid of a guidewire, through vasculature of the subject, such as (a) via the femoral vein, through inferior vena cava 74, and into right atrium 81, (b) via the basilic vein, through the subclavian vein through superior vena cava 76, and into right atrium 81, or (c) via the external jugular vein, through the subclavian vein through superior vena cava 76, and into right atrium 81. The procedure is typically performed with the aid of imaging, such as fluoroscopy, transesophageal, transthoracic echocardiography, IVUS, and/or echocardiography. The procedure may be performed using techniques described in US Patent Application Publication 2012/0035712, which is assigned to the assignee of the present application and is incorporated herein by reference, with reference to FIGS. 1A-D thereof, mutatis mutandis.

Distal end 612 of inner shaft 382 of multiple-anchor delivery tool 600 is advanced into a body of a subject, while (a) first and second tissue anchors 352A and 352B are removably positioned in inner shaft 382 at first and second longitudinal locations 614 and 616, respectively, first longitudinal location 614 more distal than second longitudinal location 616. Portion 630 of first torque cable 620 is removably positioned alongside second tissue anchor 352B in inner shaft 382. Thus, inner shaft 382 does not need to be withdrawn and reintroduced from the body during the implantation procedure.

As shown in FIG. 12A, first tissue anchor 352A is implanted into tissue 700 of the subject (e.g., cardiac muscle tissue, such as atrial tissue) by rotating first torque cable 620, using control handle 770, and, typically pushing distally on the torque cable.

As shown in FIG. 12B, after first tissue anchor 352A has been fully implanted in tissue 700, first torque cable 620 is decoupled from first tissue anchor 352A, such as by proximally withdrawing sharpened wire 642, as described hereinabove with reference to FIG. 11. First torque cable 620 is typically further proximally withdrawn in inner shaft 382 (not shown), and optionally withdrawn out of the proximal end of the inner shaft.

As shown in FIG. 12C, after first tissue anchor 352A is implanted, second tissue anchor 352B is distally advanced in inner shaft 382, and implanted into tissue 700 by rotating second torque cable 622. The second torque cable is decoupled from second tissue anchor 352B (not shown). First and second tissue anchors 352A and 352B remain implanted in tissue 700, connected by tether 350.

Tether 350 may be tensioned so as to apply tension between the first and the second tissue anchors, such as described hereinabove with reference to FIGS. 6A-C. For example, flexible longitudinal guide member 390 may be removably coupled to looped middle portion 88 of tether 350 by loop 780, such as a ring, which is connected to first flexible-longitudinal-member-coupling element 682, which may be coupled to the female part of the locking mechanism using a separate catheter delivery system, such as described in above-mentioned US Patent Application Publication 2013/0018459, for example with reference to FIGS. 25-26 thereof. After tether 350 is tensioned, tether-securing device 330 is deployed to its one-way-locked configuration, in order to maintain the tension, using outer shaft 384, as described hereinabove with reference to FIG. 6C. Once the tension has been applied, tether-securing device 330 maintains the tension.

The scope of the present invention includes embodiments described in the following applications, which are assigned to the assignee of the present application and are incorporated herein by reference. In an embodiment, techniques and apparatus described in one or more of the following applications are combined with techniques and apparatus described herein:

U.S. Pat. No. 8,475,525 to Maisano et al.;

International Application PCT/IL2011/000064, filed Jan. 20, 2011, which published as PCT Publication WO 2011/089601, and U.S. application Ser. No. 13/574,088 in the national stage thereof, which published as US Patent Application Publication 2013/0046380;

U.S. application Ser. No. 13/188,175, filed Jul. 21, 2011, which published as US Patent Application Publication 2012/0035712;

U.S. application Ser. No. 13/485,145, filed May 31, 2012, which published as US Patent Application Publication 2013/0325115;

U.S. application Ser. No. 13/553,081, filed Jul. 19, 2012, which published as US Patent Application Publication 2013/0018459;

International Application PCT/IL2012/000282, filed Jul. 19, 2012, which published as PCT Publication WO 2013/011502;

U.S. Provisional Application 61/750,427, filed Jan. 9, 2013;

U.S. Provisional Application 61/783,224, filed Mar. 14, 2013;

International Application PCT/IL2013/050470, filed May 30, 2013, which published as PCT Publication WO 2013/179295;

U.S. Provisional Application 61/897,509, filed Oct. 30, 2013;

U.S. application Ser. No. 14/143,355, filed Dec. 30, 2013, which published as US Patent Application Publication 2014/0114390;

International Application PCT/IL2014/050027, filed Jan. 9, 2014, which published as PCT Publication WO 2014/108903;

International Application PCT/IL2014/050233, filed Mar. 9, 2014, which published as PCT Publication WO 2014/141239; and U.S. Provisional Application 62/014,397; filed Jun. 19, 2014.

In particular, the stents described herein may be used as one or more of the stents described in the above-listed applications, in combination with the other techniques described therein.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising:
   a tether-securing device, which comprises a tubular element, which is shaped so as define a lateral wall that entirely surrounds a lumen, wherein the lateral wall is shaped so as to define (a) a one-way locking opening and (b) first and second non-constraining openings at respective different circumferential locations;
   at least one tether, which (a) has at least first and second tether end portions, and (b) passes through the lumen, the one-way locking opening, and the first and the second non-constraining openings; and
   first and second tissue anchors, connected to the first and the second tether end portions, respectively,
   wherein the one-way locking opening is configured to (a) allow sliding of the at least one tether in a first direction through the one-way locking opening, and (b) inhibit sliding of the at least one tether in a second direction opposite the first direction, and
   wherein the first and the second non-constraining openings are sized and shaped to allow free sliding therethrough of two longitudinal portions, respectively, of the at least one tether.

2. The apparatus according to claim 1, wherein the one-way locking opening is shaped as a slit.

3. The apparatus according to claim 1, wherein the first direction is from inside the tubular element to outside the tubular element.

4. The apparatus according to claim 1, wherein the one-way locking opening has uneven edges that are jagged or serrated.

5. The apparatus according to claim 1,
   wherein a single tether of the at least one tether has the first and the second tether end portions,
   wherein the single tether comprises at least the following non-overlapping longitudinal portions disposed in sequence along the single tether:
   the first tether end portion,
   a first portion that passes through the securing-device lumen and the one-way locking opening,
   a looped middle portion that extends out of and away from the one-way locking opening, and then loops back to the one-way locking opening,
   a second portion that passes through the securing-device lumen and the one-way locking opening, and
   the second tether end portion, and
   wherein the two longitudinal portions of the at least one tether are two longitudinal portions of the single tether, respectively, and wherein the single tether passes through the first and the second non-constraining openings.

6. The apparatus according to claim 5, further comprising a fixation tether, which is connected to the looped middle portion of the single tether.

7. The apparatus according to claim 6, further comprising a venous tissue anchor, which is configured to be implanted in a vein selected from the group of veins consisting of: an inferior vena cava, a superior vena cava, and a coronary sinus, wherein the fixation tether is connected to the venous tissue anchor and the at least one tether.

8. The apparatus according to claim 1,
wherein the at least one tether comprises first and second tethers, which (a) have the first and the second tether end portions, respectively, and (b) pass through (i) the lumen and (ii) the one-way locking opening,
wherein the one-way locking opening is configured to (a) allow the sliding of the first and the second tethers in the first direction through the one-way locking opening, and (b) inhibit the sliding of the first and the second tethers in the second direction,
wherein the two longitudinal portions of the at least one tether are a longitudinal portion of the first tether and a longitudinal portion of the second tether, respectively, and
wherein the first and the second tethers pass through the first and the second non-constraining openings, respectively, which are sized and shaped to allow free sliding therethrough of the first and the second tethers, respectively.

9. The apparatus according to claim 1, further comprising:
a venous tissue anchor, which is configured to be implanted in a vein selected from the group of veins consisting of: an inferior vena cava, a superior vena cava, and a coronary sinus; and
a fixation tether, which is connected to the venous tissue anchor and the at least one tether.

10. The apparatus according to claim 9, wherein the venous tissue anchor comprises a stent.

11. The apparatus according to claim 1, wherein the tubular element is cylindrical.

12. Apparatus comprising:
a tether-securing device, which comprises a cylindrical tubular element, which is shaped so as define a lateral wall that entirely surrounds a lumen, wherein the lateral wall is shaped so as to define a one-way locking opening;
at least one tether, which (a) has at least a first tether end portion, and (b) passes through the lumen and the one-way locking opening; and
a first tissue anchor connected to the first tether end portion,
wherein the one-way locking opening is configured to (a) allow sliding of the at least one tether in a first direction through the one-way locking opening, and (b) inhibit sliding of the at least one tether in a second direction opposite the first direction,
wherein the apparatus further comprises a second tissue anchor that comprises a head and a tissue-coupling element, and wherein the tether-securing device is fixed to the head, such that the tether-securing device surrounds at least a portion of the head, and
wherein the lateral wall is shaped so as to define a non-constraining opening, and wherein the at least one tether passes through the non-constraining opening, which is sized and shaped to allow free sliding therethrough of the at least one tether.

13. The apparatus according to claim 12, wherein the tether-securing device is configured to rotate with respect to the head.

14. The apparatus according to claim 12, wherein the one-way locking opening is shaped as a slit.

15. The apparatus according to claim 12, wherein the first direction is from inside the tubular element to outside the tubular element.

16. The apparatus according to claim 12, wherein the one-way locking opening has uneven edges that are jagged or serrated.

17. A method comprising:
delivering, to a vicinity of an anatomical site of a subject:
(a) a tether-securing device, which includes a tubular element, which is shaped so as define a lateral wall that entirely surrounds a lumen, wherein the lateral wall is shaped so as to define (i) a one-way locking opening and (ii) first and second non-constraining openings at respective different circumferential locations,
(b) at least one tether, which (i) has a first and second tether end portions, and (ii) passes through the lumen, the one-way locking opening, and the first and the second non-constraining openings, wherein the one-way locking opening is configured to (i) allow sliding of the at least one tether in a first direction through the one-way locking opening, and (ii) inhibit sliding of the at least one tether in a second direction opposite the first direction, and wherein the first and the second non-constraining openings are sized and shaped to allow free sliding therethrough of two longitudinal portions, respectively, the at least one tether, and
(c) first and second tissue anchors connected to the first and the second tether end portions, respectively;
implanting the first and the second tissue anchors in tissue of the subject; and
tensioning the at least one tether by sliding the at least one tether in the first direction through the one-way locking opening and the first and the second non-constraining openings.

18. The method according to claim 17,
wherein a single tether of the at least one tether has the first and the second tether end portions,
wherein the single tether includes at least the following non-overlapping longitudinal portions disposed in sequence along the single tether:
the first tether end portion,
a first portion that passes through the securing-device lumen and the one-way locking opening,
a looped middle portion that extends out of and away from the one-way locking opening, and then loops back to the one-way locking opening,
a second portion that passes through the securing-device lumen and the one-way locking opening, and
the second tether end portion,
wherein the two longitudinal portions of the at least one tether are two longitudinal portions of the single tether, respectively, and wherein the single tether passes through the first and the second non-constraining openings, and
wherein tensioning the at least one tether comprises proximally sliding the first and the second portions of the single tether through the one-way locking opening in the first direction by pulling, in the first direction, on the looped middle portion.

19. The method according to claim 18, further comprising connecting a fixation tether to the looped middle portion of the single tether.

20. The method according to claim 19, further comprising implanting a venous tissue anchor, which is connected to the fixation tether, in a vein selected from the group of veins consisting of: an inferior vena cava, a superior vena cava, and a coronary sinus.

21. The method according to claim 17,
wherein the at least one tether includes first and second tethers, which (a) have the first and the second tether end portions, respectively, and (b) pass through (i) the lumen and (ii) the one-way locking opening,
wherein the one-way locking opening is configured to (a) allow the sliding of the first and the second tethers in the first direction through the one-way locking opening, and (b) inhibit the sliding of the first and the second tethers in the second direction,
wherein the two longitudinal portions of the at least one tether are a longitudinal portion of the first tether and a longitudinal portion of the second tether, respectively, and wherein the first and the second tethers pass through the first and the second non-constraining openings, respectively, which are sized and shaped to allow free sliding therethrough of the first and the second tethers, respectively, and
wherein tensioning the at least one tether comprises tensioning the first and the second tethers by sliding the first and the second tethers (a) in the first direction through the one-way locking opening and (b) through the first and the second non-constraining openings, respectively.

22. The method according to claim 17, wherein the one-way locking opening is shaped as a slit.

23. The method according to claim 17, wherein the first direction is from inside the tubular element to outside the tubular element.

24. The method according to claim 17, wherein the one-way locking opening has uneven edges that are jagged or serrated.

25. The method according to claim 17, further comprising:
implanting a venous tissue anchor in a vein selected from the group of veins consisting of: an inferior vena cava, a superior vena cava, and a coronary sinus; and
connecting, to the at least one tether, a fixation tether which is connected to the venous tissue anchor.

26. The method according to claim 17, wherein the tubular element is cylindrical.

27. A method comprising:
delivering, to a vicinity of an anatomical site of a subject:
(a) a tether-securing device, which includes a cylindrical tubular element, which is shaped so as define a lateral wall that entirely surrounds a lumen, wherein the lateral wall is shaped so as to define a one-way locking opening,
(b) at least one tether, which (i) has at least a first tether end portion, and (ii) passes through the lumen and the one-way locking opening, wherein the one-way locking opening is configured to (i) allow sliding of the at least one tether in a first direction through the one-way locking opening, and (ii) inhibit sliding of the at least one tether in a second direction opposite the first direction, and
(c) a first tissue anchor connected to the first tether end portion;
implanting the first tissue anchor in tissue of the subject; and
delivering a second tissue anchor that includes a head and a tissue-coupling element, and wherein the tether-securing device is fixed to the head, such that the tether-securing device surrounds at least a portion of the head,
wherein the lateral wall is shaped so as to define a non-constraining opening, which is sized and shaped to allow free sliding therethrough of the at least one tether,
tensioning the at least one tether by sliding the at least one tether (a) in the first direction through the one-way locking opening and (b) through the non-constraining opening.

28. The method according to claim 27, wherein the tether-securing device is configured to rotate with respect to the head.

29. The method according to claim 27, wherein the one-way locking opening is shaped as a slit.

30. The method according to claim 27, wherein the first direction is from inside the tubular element to outside the tubular element.

31. The method according to claim 27, wherein the one-way locking opening has uneven edges that are jagged or serrated.

* * * * *